us008206906B2

(12) United States Patent
Zhao et al.

(10) Patent No.: US 8,206,906 B2
(45) Date of Patent: *Jun. 26, 2012

(54) **METHODS AND COMPOSITIONS FOR ANALYZING *AHASL* GENES**

(75) Inventors: Chengyan Zhao, Cary, NC (US); Robert Ascenzi, Cary, NC (US); Bijay K. Singh, Cary, NC (US)

(73) Assignee: BASF SE, Ludwigshafen (DE)

( * ) Notice: Subject to any disclaimer, the term of this patent is extended or adjusted under 35 U.S.C. 154(b) by 592 days.

This patent is subject to a terminal disclaimer.

(21) Appl. No.: 12/205,246

(22) Filed: Sep. 5, 2008

(65) Prior Publication Data

US 2009/0029381 A1    Jan. 29, 2009

Related U.S. Application Data

(62) Division of application No. 10/805,973, filed on Mar. 22, 2004, now Pat. No. 7,432,082.

(51) Int. Cl.
*C12Q 1/68*     (2006.01)
*C12P 19/34*    (2006.01)
*C07H 21/02*    (2006.01)
*C07H 21/04*    (2006.01)

(52) U.S. Cl. ....... 435/6.1; 435/91.2; 536/23.1; 536/24.3

(58) Field of Classification Search .................. None
See application file for complete search history.

(56) References Cited

U.S. PATENT DOCUMENTS

| | | | |
|---|---|---|---|
| 5,595,890 | A | 1/1997 | Newton et al. |
| 5,858,652 | A | 1/1999 | Laffler et al. |
| 5,876,932 | A | 3/1999 | Fischer |
| 6,225,105 | B1 | 5/2001 | Sathasivan et al. |
| 6,339,184 | B1 | 1/2002 | Smith |
| 6,475,736 | B1 | 11/2002 | Stanton |
| 6,627,401 | B2 | 9/2003 | Ralhan |
| 2002/0138881 | A1 | 9/2002 | Charne et al. |
| 2003/0096277 | A1 | 5/2003 | Chen |
| 2003/0138780 | A1 | 7/2003 | Gill et al. |
| 2004/0142353 | A1 | 7/2004 | Cheung et al. |
| 2009/0098552 | A1* | 4/2009 | Zhao et al. ........... 435/6 |

FOREIGN PATENT DOCUMENTS

| | | |
|---|---|---|
| WO | WO 01/92512 A2 | 12/2001 |
| WO | WO 03/013225 A2 | 2/2003 |
| WO | WO 03/014356 A1 | 2/2003 |
| WO | WO 03/014357 A1 | 2/2003 |
| WO | WO 03014357 A1 | 2/2003 |
| WO | WO 03/076574 A2 | 9/2003 |
| WO | WO 2004/016073 A2 | 2/2004 |
| WO | WO 2004/040012 A2 | 5/2004 |

OTHER PUBLICATIONS

Ascenzi, R., et al., (2003) International Society of Plant Molecular Biologists Congress, Barcelona, Spain, Ref. No. S10-17.
Ayyadevara, S., et al., "Discrimination of Primer 3'-Nucleotide Mismatch by *Taq* DNA Polymerase during Polymerase Chain Reaction," *Analytical Biochemistry*, 2000, pp. 11-18, vol. 284, Academic Press.
Chang, A. and Duggleby, R., "Herbicide-resistant forms of *Arabidopsis thaliana* acetohydroxyacid synthase: characterization of the catalytic properties and sensitivity to inhibitors of four defined mutants," *Biochemistry Journal*, 1998, pp. 765-777, vol. 333.
Delrio-Lafreniere SA et al., "Simultaneous allele-specific amplification: a strategy using modified primer-template mismatches for SNP detection—application to prothrombin 20210A (factor II) and factor V Leiden (1691A) gene mutations" *Molecular Diagnostics*, 2001, pp. 201-209, vol. 6., No. 3.
Hattori, J., et al., "An Acetohydroxyacid Synthase Mutant Reveals a Single Site Involved in Multiple Herbicide Resistance," *Molecular and General Genetics*, 1995, pp. 419-425, vol. 246, Springer Verlag, Berlin, Germany.
Hattori, J., et al., "Multiple resistance to sulfonylureas and imidazolinones conferred by an acetohydroxyacid synthase gene with separate mutations for selective resistance," *Molecular Genetics*, 1992, pp. 167-173, vol. 232.
Kwok, S., et al., "Effects of primer-templates mismatches on the polymerase chain reaction: human immunodeficiency virus type 1 model studies" *Nucleic Acids Res.* Feb. 25, 1990; 18(4):999-1005.
Lee, I., et al., "Guidelines for incorporating non-perfectly matched oligonucleotides into target-specific hybridization probes for DNA microarray," *Nucleic Acids Research*, 2004, pp. 681-690, vol. 32, Oxford University Press.
Liu, Q., et al., "Overlapping PCR for bidirectional PCR amplification of specific alleles: a rapid one-tube method for simultaneously differentiating homozygotes and heterozygotes" *Genome Res.* Apr. 1997; 7(4):389-98.
Newton, C., et al., "Analysis of any point mutation in DNA. The amplification refractory mutation system (ARMS)," *Nucleic Acids Research*, 1989, pp. 2503-2516, vol. 17, No. 7, Oxford University Press.
Pettersson, M., et al., "Molecular haplotype determination using allele-specific PCR and Pyrosequencing technology," *Genomics*, 2003, pp. 390-396, vol. 82, Elsevier Science.
Pozniak, C.J., et al., "Physiological and Molecular Characterization of Mutation-Derived Imidazolinone Resistance in Spring Wheat," 2004, *Crop Science*, 2004, pp. 1434-1443, vol. 44(4).
Sathasivan, K., et al., "Nucleotide sequence of a mutant acetolactate synthase gene from an imidaziolinone-resistance *Arabidopsis thaliana* var. Columbia," *Nucleic Acids Research*, 1990, p. 2188, vol. 18, No. 8, Oxford University Press.
Sathasivan, K., et al., "Molecular Basis of Imidazolinone Herbicide Resistance in *Arabidopsis thaliana* var. Columbia," *Plant Physiology*, 1991, pp. 1044-1050, vol. 97.
See, D., et al., "Electophoretic Detection of Single-Nucleotide Polymorphisms," *BioTechniques*, 2000, pp. 710-716, vol. 28.

(Continued)

*Primary Examiner* — Stephen Kapushoc
(74) *Attorney, Agent, or Firm* — Womble Carlyle Sandridge & Rice LLP

(57) ABSTRACT

The invention relates to methods and compositions for analyzing plant acetohydroxy acid synthase large subunit (AHASL) genes. In particular, the invention relates to methods for the detection of wild-type AHASL alleles and mutant AHASL alleles that encode imidazolinone-tolerant AHASL proteins. The methods involve the use of PCR amplification and novel compositions comprising allele-specific and gene-specific primers to detect the presence of mutant and/or wild-type alleles present at the individual AHASL genes of a plant. Specifically, the methods and compositions are useful for analyzing the three AHASL genes of *Triticum aestivum* and the two AHASL genes of *Triticum turgidum* ssp. *durum*.

25 Claims, 10 Drawing Sheets

OTHER PUBLICATIONS

Stein, N., et al., "A new DNA extraction method for high-throughput marker analysis in a large-genome species such as *Triticum aestivum*," *Plant Breeding*, 2001, pp. 354-356, vol. 120, Blackwell Wissenschafts-Verlag, Germany.

Werle, E. et al., "Convenient single-step, one tube purification of PCR products for direct sequencing" *Nucleic Acids Research*, 1994, pp. 4354-4355, vol. 22, No. 20.

Wu, D., et al., "Allele-specific enzymatic amplification of β-globin genomic DNA for diagnosis of sickle cell anemia," *Proceedings of the National Academy of Sciences USA*, 1989, pp. 2757-2760, vol. 86.

* cited by examiner

FIGURE 1

A  *AHASL1D*

WT
```
CACGTGCTGCCTATGATCCCAAGCGGTGGTGCTTTCAAGGAC
 H   V   L   P   M   I   P   S   G   G   A   F   K   D
```
MUT
```
CACGTGCTGCCTATGATCCCAAACGGTGGTGCTTTCAAGGAC
 H   V   L   P   M   I   P   N   G   G   A   F   K   D
```

B  *AHASL1B*

WT
```
CACGTGCTGCCTATGATCCCAAGCGGTGGTGCTTTTAAGGAC
 H   V   L   P   M   I   P   S   G   G   A   F   K   D
```
MUT
```
CACGTGCTGCCTATGATCCCAAACGGTGGTGCTTTTAAGGAC
 H   V   L   P   M   I   P   N   G   G   A   F   K   D
```

C  *AHASL1A*

WT
```
CACGTGCTGCCTATGATCCCAAGCGGTGGTGCTTTCAAGGAC
 H   V   L   P   M   I   P   S   G   G   A   F   K   D
```
MUT
```
CACGTGCTGCCTATGATCCCAAACGGTGGTGCTTTCAAGGAC
 H   V   L   P   M   I   P   N   G   G   A   F   K   D
```

```
» AHASL1B  (1651)  TGGTGGTGCAGTGGGAGGATAGGTTTTACAAGGCCAACCGGGCGCACACA
» AHASL1D  (1345)  TGGTGGTGCAGTGGGAGGATAGGTTTTACAAGGCCAATCGGGCGCACACA
» AHASL1A  (1458)  TGGTGGTGCAATGGGAGGATAGGTTTTACAAGGCCAATCGGGCGCACACA
          (1651)                              +              +

» AHASL1B  (1701)  TACCTTGGCAACCCAGAAAATGAGAGTGAGATATATCCAGATTTTGTGAC
» AHASL1D  (1395)  TACCTTGGCAACCCAGAAAATGAGAGTGAGATATATCCAGATTTTGTGAC
» AHASL1A  (1508)  TACCTTGGCAACCCAGAAAATGAGAGTGAGATATATCCAGATTTTGTGAC
          (1701)

» AHASL1B  (1751)  GATTGCTAAAGGATTCAACGTTCCGGCAGTTCGTGTGACGAAGAAGAGCG
» AHASL1D  (1445)  GATTGCTAAAGGATTCAACGTTCCAGCAGTTCGAGTGACGAAGAAGAGCG
» AHASL1A  (1558)  GATTGCTAAAGGATTCAACGTTCCGGCAGTTCGTGTGACGAAGAAGAGCG
          (1751)                        +         +

» AHASL1B  (1801)  AAGTCACTGCAGCAATCAAGAAGATGCTTGAGACCCCAGGGCCATACTTG
» AHASL1D  (1495)  AAGTCACTGCAGCAATCAAGAAGATGCTTGAGACCCCAGGGCCATACTTG
» AHASL1A  (1608)  AAGTCACTGCAGCAATCAAGAAGATGCTTGAGACCCCAGGGCCATACTTG
          (1801)

» AHASL1B  (1851)  TTGGATATCATTGTCCCGCATCAGGAGCACGTGCTGCCTATGATCCCAAG
» AHASL1D  (1545)  TTGGATATCATAGTCCCGCATCAGGAGCACGTGCTGCCTATGATCCCAAG
» AHASL1A  (1658)  TTGGATATCATCGTCCCGCATCAGGAGCACGTGCTGCCTATGATCCCAAG
          (1851)             +

» AHASL1B  (1901)  CGGTGGTGCTTTTAAGGACATGATCATGGAGGGTGATGGCAGGACCTCGT
» AHASL1D  (1595)  CGGTGGTGCTTTCAAGGACATGATCATGGAGGGTGATGGCAGGACCTCGT
» AHASL1A  (1708)  CGGTGGTGCTTTCAAGGACATGATCATGGAGGGTGATGGCAGGACCTCGT
          (1901)              +

» AHASL1B  (1951)  ACTGAAATTTCGACCTACAAGACCTACAAGTGTGACATGCGCAATCAGCA
» AHASL1D  (1645)  ACTGAAATTTCGACCTACAAGACCTACAAGTGTGACATGCGCAATCAGCA
» AHASL1A  (1758)  ACTGAAATTTCGACCTACAAGACCTACAAGTGTGACATGCGCAATCAGCA
          (1951)

» AHASL1B  (2001)  TGATACCTGCGTGTTGTATCAACTACTGGGGGTTCAACTGTGAACCATGC
» AHASL1D  (1695)  TGATGCCCGCGTGTTGTATCAACTACTAGGGGTTCAACTGTGARCCATGC
» AHASL1A  (1808)  TGGTGCCCGCGTGTTGTATCAACTACTAGGGGTTCAACTGTGAACCATGC
          (2001)    + + +                    +               +

» AHASL1B  (2051)  GTTTTCTAGTTTGCTTGTTTCATTCATATAAGCTTGTGTTACTTAGTTCC
» AHASL1D  (1745)  GTTTTCTAGTTTGCTTGTTTCATTCATATAAGCTTGTRTTACTTAGTTCC
» AHASL1A  (1858)  GTTTTCTAGTTTGCTTGTTTCATTCATATAAGCTTGTGTTACTTAGTTCC
          (2051)                                       +
```

```
» AHASL1B  (2101)  GAACCGTGTAGTTTTGTAGTCTCTGTTCTCTTTTGTAGGGAYGTGCTGTC
» AHASL1D  (1795)  GAACCCTGTAGTTTTGTAGTCTATGTTCTCTTTTGTAGGGATGTGCTGTC
» AHASL1A  (1908)  GAACCCTGTAGCTTTGTAGTCTATGCTATCTTTTGTAGGGATGTGCTGTC
           (2101)       +      +         +  + +          +

» AHASL1B  (2151)  ATAARATATCATGCAAGTTTCTTGTCCTACATATCAATAATAAGCACTTC
» AHASL1D  (1845)  ATAARATRTCATGCAAGTTTCTTGTCCTACATATCAATAATAAGTACTTC
» AHASL1A  (1958)  ATAAAATATCATGCAAGTTTCTTGTCCTACATATCAATAATAAGTACTTC
«  CM-R       (1)
           (2151)      + +                                     +

» AHASL1B  (2201)  CATGGAGCAAAAAAAAAAAAAAAAAAAAAAAAAA
» AHASL1D  (1895)  CATGCAGTAAAAAAAAAAAAAAAAAAAAAAAAAA
» AHASL1A  (2008)  CATGGAAAAAAAAAAAAAAAAAAAAAAAAAAAAA
           (2201)      + ++
```

```
» AHASL1B  (1301) AGGATTCAAGACTTTTGGTGAGGCCATCCCGCCGCAATATGCTATCCAGG
» AHASL1D   (995) AGGATTCAAGACTTTTGGCGAGGCCATCCCGCCGCAATATGCTATCCAGG
» AHASL1A  (1108) AGGATTCAAGACTTTTGGCGAGGCCATCCCGCCGCAATATGCTATCCAGG
           (1301)                  +

» 1AD-F    (1)                                 GGGAGGCGATCATTGCCAC
» AHASL1B  (1351) TACTGGATGAGCTGACAAAAGGGGAGGCGATCATTGCCACCGGTGTTGGG
» AHASL1D  (1045) TACTGGATGAGCTGACAAAAGGGGAGGCGATCATTGCCACTGGTGTTGGG
» AHASL1A  (1158) TACTGGATGAGCTGACAAAAGGGGAGGCGATCATTGCTACTGGTGTTGGG
           (1351)                                          +  +

» 1B-F    (1)                                                GGCA
» AHASL1B  (1401) CAGCATCAGATGTGGGCGGCTCAGTATTACACTTACAAGCGGCCACGGCA
» AHASL1D  (1095) CAGCACCAGATGTGGGCGGCTCAGTATTACACTTACAAGCGGCCACGGCA
» AHASL1A  (1208) CAGCACCAGATGTGGGCGGCTCAGTATTACACTTACAAGCGGCCACGGCA
           (1401)     +

» 1B-F    (6) CTGGCTGTCTTCATCC
» AHASL1B  (1451) GTGGCTGTCTTCATCCGGTTTGGGTGCAATGGGATTTGGGTTGCCAGCTG
» AHASL1D  (1145) GTGGCTGTCTTCGTCTGGTTTGGGGGCAATGGGATTTGGGTTACCAGCTG
» AHASL1A  (1258) GTGGCTGTCTTCGTCTGGTTTGGGGGCAATGGGATTTGGGTTACCAGCTG
           (1451)             +  +            +                  +

» AHASL1B  (1501) CAGCTGGCGCTGCTGTGGCCAACCCAGGTGTTACAGTTGTTGACATTGAT
» AHASL1D  (1195) CAGCTGGCGCTGCTGTGGCCAACCCAGGTGTTACAGTTGTTGACATTGAT
» AHASL1A  (1308) CAGCTGGCGCTGCTGTGGCCAACCCAGGTGTTACAGTTGTTGACATTGAT
           (1501)

» AHASL1B  (1551) GGGGATGGTAGTTTCCTCATGAACATTCAGGAGTTGGCGTTGATCCGTAT
» AHASL1D  (1245) GGTGATGGTAGTTTCCTCATGAACATTCAGGAGTTGGCGTTGATCCGCAT
» AHASL1A  (1358) GGAGATGGTAGTTTCCTCATGAACATTCAGGAGTTGGCATTGATCCGTAT
           (1551) +                                     +         +

» AHASL1B  (1601) TGAGAACCTCCCAGTGAAGGTGATGATATTGAACAACCAGCATCTGGGAA
» AHASL1D  (1295) TGAGAACCTCCCAGTGAAGGTGATGATATTGAACAACCAGCATCTGGGAA
» AHASL1A  (1408) TGAGAACCTCCCTGTGAAGGTGATGATATTGAACAACCAGCATCTGGGAA
           (1601)             +

« 1A-R    (1)
» AHASL1B  (1651) TGGTGGTGCAGTGGGAGGATAGGTTTTACAAGGCCAACCGGGCGCACACA
» AHASL1D  (1345) TGGTGGTGCAGTGGGAGGATAGGTTTTACAAGGCCAATCGGGCGCACACA
» AHASL1A  (1458) TGGTGGTGCAATGGGAGGATAGGTTTTACAAGGCCAATCGGGCGCACACA
           (1651)           +                          +
```

```
» AHASL1B  (2101)  GAACCGTGTAGTTTTGTAGTCTCTGTTCTCTTTTGTAGGGAYGTGCTGTC
» AHASL1D  (1795)  GAACCCTGTAGTTTTGTAGTCTATGTTCTCTTTTGTAGGGATGTGCTGTC
» AHASL1A  (1908)  GAACCCTGTAGCTTTGTAGTCTATGCTATCTTTTGTAGGGATGTGCTGTC
    « 1D-R    (1)
    « 1A-R    (1)
           (2101)      +       +        + ++  +           +

» AHASL1B  (2151)  ATAARATATCATGCAAGTTTCTTGTCCTACATATCAATAATAAGCACTTC
» AHASL1D  (1845)  ATAARATRTCATGCAAGTTTCTTGTCCTACATATCAATAATAAGTACTTC
» AHASL1A  (1958)  ATAAAATATCATGCAAGTTTCTTGTCCTACATATCAATAATAAGTACTTC
           (2151)     + +                                    +

» AHASL1B  (2201)  CATGGAGCAAAAAAAAAAAAAAAAAAAAAAAA
» AHASL1D  (1895)  CATGCAGTAAAAAAAAAAAAAAAAAAAAAAAA
» AHASL1A  (2008)  CATGGAAAAAAAAAAAAAAAAAAAAAAAAAAA
```

FIGURE 6

|  | Hexaploid L1D | Hexaploid L1B | Hexaploid L1A | Tetraploid L1B | Tetraploid L1A |
|---|---|---|---|---|---|
| Hexaploid L1D | 100% | | | | |
| Hexaploid L1B | 97.8% | 100% | | | |
| Hexaploid L1A | 98.2% | 97.7% | 100% | | |
| Tetraploid L1B | 97.4% | 99.4% | 97.3% | 100% | |
| Tetraploid L1A | 97.8% | 97.3% | 99.6% | 97.6% | 100% |

METHODS AND COMPOSITIONS FOR ANALYZING *AHASL* GENES

CROSS-REFERENCE TO RELATED APPLICATIONS

This application is a division of U.S. application Ser. No. 10/805,973, filed Mar. 22, 2004, which is hereby incorporated herein in its entirety by reference.

FIELD OF THE INVENTION

This invention relates to the field of gene analysis, particularly to novel methods for the identification of wild-type and herbicide-tolerant alleles of plant AHASL genes.

BACKGROUND OF THE INVENTION

Acetohydroxyacid synthase (AHAS; EC 4.1.3.18, also known as acetolactate synthase or ALS), is the first enzyme that catalyzes the biochemical synthesis of the branched-chain amino acids valine, leucine and isoleucine (Singh (1999) "Biosynthesis of valine, leucine and isoleucine," in *Plant Amino Acids*, Singh, B. K., ed., Marcel Dekker Inc. New York, N.Y., pp. 227-247). AHAS is the site of action of four structurally diverse herbicide families including the sulfonylureas (LaRossa and Falco (1984) *Trends Biotechnol.* 2:158-161), the imidazolinones (Shaner et al. (1984) *Plant Physiol.* 76:545-546), the triazolopyrimidines (Subramanian and Gerwick (1989) "Inhibition of acetolactate synthase by triazolopyrimidines," in *Biocatalysis in Agricultural Biotechnology*, Whitaker, J. R. and Sonnet, P. E. eds., ACS Symposium Series, American Chemical Society, Washington, D.C., pp. 277-288), and the pyrimidyloxybenzoates (Subramanian et al. (1990) *Plant Physiol.* 94: 239-244.). Imidazolinone and sulfonylurea herbicides are widely used in modern agriculture due to their effectiveness at very low application rates and relative non-toxicity in animals. By inhibiting AHAS activity, these families of herbicides prevent further growth and development of susceptible plants including many weed species. Several examples of commercially available imidazolinone herbicides are PURSUIT® (imazethapyr), SCEPTER® (imazaquin) and ARSENAL® (imazapyr). Examples of sulfonylurea herbicides are chlorsulfuron, metsulfuron methyl, sulfometuron methyl, chlorimuron ethyl, thifensulfuron methyl, tribenuron methyl, bensulfuron methyl, nicosulfuron, ethametsulfuron methyl, rimsulfuron, triflusulfuron methyl, triasulfuron, primisulfuron methyl, cinosulfuron, amidosulfiuon, fluzasulfuron, imazosulfuron, pyrazosulfuron ethyl and halosulfuron.

Due to their high effectiveness and low-toxicity, imidazolinone herbicides are favored for application by spraying over the top of a wide area of vegetation. The ability to spray an herbicide over the top of a wide range of vegetation decreases the costs associated with plantation establishment and maintenance, and decreases the need for site preparation prior to use of such chemicals. Spraying over the top of a desired tolerant species also results in the ability to achieve maximum yield potential of the desired species due to the absence of competitive species. However, the ability to use such spray-over techniques is dependent upon the presence of imidazolinone-resistant species of the desired vegetation in the spray over area.

Among the major agricultural crops, some leguminous species such as soybean are naturally resistant to imidazolinone herbicides due to their ability to rapidly metabolize the herbicide compounds (Shaner and Robinson (1985) *Weed Sci.* 33:469-471). Other crops such as corn (Newhouse et al. (1992) *Plant Physiol.* 100:882886) and rice (Barrett et al. (1989) *Crop Safeners for Herbicides*, Academic Press, New York, pp. 195-220) are somewhat susceptible to imidazolinone herbicides. The differential sensitivity to the imidazolinone herbicides is dependent on the chemical nature of the particular herbicide and differential metabolism of the compound from a toxic to a non-toxic form in each plant (Shaner et al. (1984) *Plant Physiol.* 76:545-546; Brown et al., (1987) *Pestic. Biochem. Physiol.* 27:24-29). Other plant physiological differences such as absorption and translocation also play an important role in sensitivity (Shaner and Robinson (1985) *Weed Sci.* 33:469-471).

Plants resistant to imidazolinones, sulfonylureas and triazolopyrimidines have been successfully produced using seed, microspore, pollen, and callus mutagenesis in *Zea mays*, *Arabidopsis thaliana*, *Brassica napus*, *Glycine max*, and *Nicotiana tabacum* (Sebastian et al. (1989) *Crop Sci.* 29:1403-1408; Swanson et al., 1989 *Theor. Appl. Genet.* 78:525-530; Newhouse et al. (1991) *Theor. Appl. Genet.* 83:65-70; Sathasivan et al. (1991) *Plant Physiol.* 97:1044-1050; Mourand et al. (1993) *J. Heredity* 84:91-96). In all cases, a single, partially dominant nuclear gene conferred resistance. Four imidazolinone resistant wheat plants were also previously isolated following seed mutagenesis of *Triticum aestivum* L. cv. Fidel (Newhouse et al. (1992) *Plant Physiol.* 100:882-886). Inheritance studies confirmed that a single, partially dominant gene conferred resistance. Based on allelic studies, the authors concluded that the mutations in the four identified lines were located at the same locus. One of the Fidel cultivar resistance genes was designated FS-4 (Newhouse et al. (1992) *Plant Physiol.* 100:882-886).

Computer-based modeling of the three dimensional conformation of the AHAS-inhibitor complex predicts several amino acids in the proposed inhibitor binding pocket as sites where induced mutations would likely confer selective resistance to imidazolinones (Ott et al. (1996) *J. Mol. Biol.* 263: 359-368). Wheat plants produced with some of these rationally designed mutations in the proposed binding sites of the AHAS enzyme have in fact exhibited specific resistance to a single class of herbicides (Ott et al. (1996) *J. Mol. Biol.* 263:359-368).

Plant resistance to imidazolinone herbicides has also been reported in a number of patents. U.S. Pat. Nos. 4,761,373, 5,331,107, 5,304,732, 6,211,438, 6,211,439 and 6,222,100 generally describe the use of an altered AHAS gene to elicit herbicide resistance in plants, and specifically discloses certain imidazolinone resistant corn lines. U.S. Pat. No. 5,013,659 discloses plants exhibiting herbicide resistance due to mutations in at least one amino acid in one or more conserved regions. The mutations described therein encode either cross-resistance for imidazolinones and sulfonylureas or sulfonylurea-specific resistance, but imidazolinone-specific resistance is not described. Additionally, U.S. Pat. No. 5,731,180 and U.S. Pat. No. 5,767,361 discuss an isolated gene having a single amino acid substitution in a wild-type monocot AHAS amino acid sequence that results in imidazolinone-specific resistance.

In plants, as in all other organisms examined, the AHAS enzyme is comprised of two subunits: a large subunit (catalytic role) and a small subunit (regulatory role) (Duggleby and Pang (2000) *J. Biochem. Mol. Biol.* 33:1-36). The large subunit (termed AHASL) may be encoded by a single gene as in the case of *Arabidopsis* and rice or by multiple gene family members as in maize, canola, and cotton. Specific, single-nucleotide substitutions in the large subunit confer upon the enzyme a degree of insensitivity to one or more classes of herbicides (Chang and Duggleby (1998) *Biochem J.* 333:765-777).

Mutations in genes encoding the AHAS large subunit, which are referred to herein as AHASL genes, are the molecular basis of herbicide tolerance in CLEARFIELD® crops which have increased tolerance to imidazolinone herbicides. Because each of these mutations results in a semi-dominant phenotype one mutation in a heterozygous state may be sufficient to produce a level of herbicide tolerance that is sufficient for many crop productions systems. However, for particular herbicide applications, and in cases with crop plants having multiple AHASL genes such as wheat, combinations of mutations are desired to achieve an increased level of resistance to herbicides.

For example, bread wheat, *Triticum aestivum* L., contains three homoeologous acetohydroxyacid synthase large subunit genes. Each of the genes exhibit significant expression based on herbicide response and biochemical data from mutants in each of the three genes (Ascenzi et al. (2003) International Society of Plant Molecular Biologists Congress, Barcelona, Spain, Ref. No. S10-17). The coding sequences of all three genes share extensive homology at the nucleotide level (WO 03/014357). Through sequencing the AHASL genes from several varieties of *Triticum aestivum*, the molecular basis of herbicide tolerance in most imidazolinone (IMI)-tolerant lines was found to be the mutation S653 (At)N, indicating a serine to asparagine substitution at a position equivalent to the serine at amino acid 653 in *Arabidopsis thaliana* (WO 03/01436; WO 03/014357). The S653(At)N mutation in each gene is shaded in FIGS. 1A, 1B, and 1C. This mutation is due to a single nucleotide polymorphism (SNP) in the DNA sequence encoding the AHASL protein.

One goal of plant breeders is to introduce imidazolinone tolerance into existing wheat lines by inducing the S653 (At)N mutation in the existing lines or by crossing non-IMI-tolerant lines with IMI-tolerant lines following by backcrossing and selection for imidazolinone tolerance. Another goal of plant breeders is to produce wheat plants with increased levels of imidazolinone tolerance, beyond the levels of tolerance seen in wheat plants possessing a single S653(At)N mutation in a single wheat AHASL gene. Thus, it is desirable to breed wheat plants that possess combinations of S653 (At)N mutations at two or more of the AHASL genes. In addition, it is also desirable to breed wheat plants that are homozygous for the mutant S653(At)N allele at one or more of the AHASL genes. However, to develop the desired wheat plants, rapid methods for identifying the desired plants are needed. Existing methods of detecting wheat plants with imidazolinone tolerance are not well suited for use in the development of plants that possess more than a single S653 (At)N allele at a single AHASL gene.

Existing methods of identifying plants with enhanced imidazolinone tolerance include field or greenhouse herbicide spray tests and biochemical assays for AHAS activity. Such methods are time consuming, however, and generally not suited for distinguishing, among large numbers of individual plants, subtle increases in imidazolinone tolerance that may occur when a second S653(At)N allele is introduced into a wheat plant.

Alternative methods for identifying desired plants include DNA-based methods. For example, the AHASL genes, or portions thereof, can be amplified from genomic DNA by polymerase chain reaction (PCR) methods and the resulting amplified AHASL gene or portion thereof can be sequenced to identify the mutant S653(At)N allele and the particular AHASL gene that it is present in. However, such a DNA-sequencing-based method is not practical for large numbers of samples. Another approach involves that use of radiolabelled or non-isotopically tagged, allele-specific oligonucleotides (ASOs) as probes for dot blots of genomic DNA or polymerase chain reaction (PCR) amplified DNA (Connor et al. (1983) *Proc. Natl. Acad. Sci. USA* 80:278-282; Orkin et al. (1983) *J. Clin. Invest.* 71:775-779; Brun et al. (1988) *Nucl. Acids Res.* 16:352; and Bugawan et al. (1988) *Biotechnology* 6:943-947. While such an approach is useful for distinguishing between two alleles at a single locus, this approach is not useful for the wheat AHASL genes, because three AHASL genes are nearly identical (FIG. 1) in region surround the SNP that gives rise to the mutant S653(At)N AHASL protein. Thus, a set of six oligonucleotide probes could not be developed that would be able to distinguish between the mutant and wild-type alleles at each of the three wheat AHASL genes.

One method that can be adapted for rapidly screening large numbers of individuals for the analysis of an SNP is the amplification refractory mutation system (ARMS) (Newton et al. (1989) *Nucl. Acids Res.* 17:2503-2516). This PCR-based method can be used to distinguish two alleles of a gene that differ by a single nucleotide and can also be used to distinguish heterozygotes from homozygotes for either allele by inspection of the PCR products after agarose gel electrophoresis and ethidium-bromide staining. The ARMS method is based on the premise that oligonucleotides with a mismatched 3'-residue will not function as primers in PCR under the appropriate conditions (Newton et al. (1989) *Nucl. Acids Res.* 17:2503-2516). While this method has proven useful for the analysis of an SNP at a single gene, whether this method, or a other PCR-based methods, can be used be used for the analysis of the SNP that gives rise to the S653(At)N mutation in each of the three wheat AHASL genes has not been reported.

SUMMARY OF THE INVENTION

The present invention provides methods for analyzing plant AHASL genes. The methods are directed to detecting in samples comprising plant genomic DNA the presence of the wild-type allele and/or a mutant allele at each of the AHASL genes in a plant's genome. The mutant AHASL alleles of the invention encode imidazolinone-tolerant AHASL proteins comprising the S653(At)N substitution. At the DNA-level, the mutant allele results from a G-to-A transition at the position that corresponds to nucleotide 1958 of the *Arabidopsis* AHASL nucleotide sequence set forth in EMBL Accession No. X51514. The methods are particularly directed to analyzing the AHASL genes of plants that comprise two or more AHASL genes, including, but not limited to, *Triticum aestivum* and *Triticum turgidum* ssp. *durum*.

In a first aspect, the invention provides a method for detecting a mutant allele of an AHASL gene that confers on a plant tolerance to imidazolinone herbicides. The method comprises the steps of: (a) obtaining genomic DNA from a plant, particularly a wheat plant; (b) using the DNA as a template for a PCR amplification comprising the DNA, polymerase, deoxyribonucleotide triphosphates, a forward AHASL-gene-specific primer, a reverse AHASL-gene-specific primer, and a mutant-allele-specific primer; and (c) detecting the products of the PCR amplification. The mutant-allele-specific primer comprises a nucleotide sequence with a 5' end and a 3' end, wherein the nucleotide sequence corresponds to the coding strand of an AHASL gene, the 3' end nucleotide corresponds to the site of the G-to-A point mutation, and the 3' end nucleotide is cytidine. In addition the mutant-allele-specific primer is capable of annealing to a region of an AHASL gene that is nested between the annealing sites of the forward and reverse AHASL-gene-specific primers. In an embodiment of the invention, the mutant-allele-specific primer comprises a nucleotide sequence with a 5' end and a 3' end, wherein the nucleotide sequence is capable of annealing to the complement of nucleotides 3 to 23 of SEQ ID NO: 12 and has a cytidine at the 3' end.

In a second aspect, the invention provides a method for analysis of a plant AHASL gene, particularly an AHASL gene selected from the group consisting of AHASL1D, AHASL1B, and AHASL1A of *Triticum aestivum* and the AHAS1B and AHASL1A of *Triticum turgidum* ssp. *durum*. The method comprises the steps of: (a) obtaining genomic DNA from a plant, particularly a wheat plant; (b) using the DNA as a template for a first PCR amplification comprising said DNA, polymerase, deoxyribonucleotide triphosphates, a forward AHASL-gene-specific primer, a reverse AHASL-gene-specific primer, and a mutant-allele-specific primer as described above; (c) using the DNA as a template for a second PCR amplification comprising said DNA, polymerase, deoxyribonucleotide triphosphates, the forward AHASL-gene-specific primer, the reverse AHASL-gene-specific primer, and a wild-type-allele-specific primer; and (d) detecting the products of said first and said second PCR amplifications. The wild-type-allele-specific primer comprises a nucleotide sequence with a 5' end and a 3' end, wherein the nucleotide sequence corresponds to the coding strand of an AHASL gene, the 3' end nucleotide corresponds to the site of the G-to-A point mutation, and the 3' end nucleotide is guanosine. The wild-type-allele-specific primers of the invention are capable of annealing to a region of an AHASL gene that is nested between the annealing sites of the forward and reverse AHASL-gene-specific primers. In another embodiment of the invention, the wild-type-allele-specific primer comprises a first nucleotide sequence with a 5' end and a 3' end, wherein the first nucleotide sequence is capable of annealing to the complement of nucleotides 4 to 23 of SEQ ID NO: 10 and has a guanosine at the 3' end.

In a third aspect, the invention provides a method for analysis of an AHASL gene, involving an initial PCR amplification of at least a fragment of each of the AHASL genes in a plant, so as to enrich a sample of genomic DNA for the AHASL genes or fragments thereof. The steps of the method comprise: (a) obtaining genomic DNA from a plant, particularly a wheat plant; (b) using the DNA as a template in a pre-amplification comprising the DNA, deoxyribonucleotide triphosphates, polymerase, a forward AHASL primer, and a reverse AHASL primer, so as to produce pre-amplified DNA; (c) using the pre-amplified DNA as a template for a first PCR amplification comprising the pre-amplified DNA, polymerase, deoxyribonucleotide triphosphates, a forward AHASL-gene-specific primer, a reverse AHASL-gene-specific primer, and a mutant-allele-specific primer as described above; (d) using the pre-amplified DNA as a template for a second PCR amplification comprising the pre-amplified DNA, polymerase, deoxyribonucleotide triphosphates, said forward AHASL-gene-specific primer, the reverse AHASL-gene-specific primer, and a wild-type-allele-specific primer as described above; and (e) detecting the products of said first and said second PCR amplifications. The mutant-allele-specific primer and the wild-type-allele-specific primer are capable of annealing to a region of an AHASL gene that is nested between the annealing sites of the forward and reverse AHASL-gene-specific primers. In addition, the forward and reverse AHASL-gene-specific primers are nested between the annealing sites of the forward and reverse AHASL primers.

The present invention provides the oligonucleotide primers that are described above. These primers include, but are not limited to, a mutant-allele-specific primer comprising the nucleotide sequence set forth in SEQ ID NO: 3, the wild-type-allele-specific primer comprising the nucleotide sequence set forth in SEQ ID NO: 4, the forward AHASL-gene-specific primers comprising the nucleotide sequences set forth in SEQ ID NOS: 5 and 6, the reverse AHASL-gene-specific primers comprising the nucleotide sequences set forth in SEQ ID NOS: 7, 8, and 9, the forward AHASL primer comprising the nucleotide sequence set forth in SEQ ID NO: 1, and the reverse AHASL primer comprising the nucleotide sequence set forth in SEQ ID NO: 2.

The present invention also provides kits for performing the methods of the invention as described above. Such kits comprise at least one forward AHASL-gene-specific primer, at least one reverse AHASL-gene-specific primer, a mutant-allele-specific primer, at least one polymerase enzyme capable of catalyzing the PCR amplification of a first fragment of a wheat AHASL gene and a second fragment of a wheat AHASL gene. The kits of the invention can further comprise any additional components that are required for the performing methods of the present invention as described herein.

BRIEF DESCRIPTION OF THE DRAWINGS

FIG. 1A depicts the nucleotide (SEQ ID NO: 10) and amino acid (SEQ ID NO: 11) sequences of the wild-type (WT) AHASL1D and nucleotide (SEQ ID NO: 12) and amino acid (SEQ ID NO: 13) sequences of the mutant (MUT) AHASL1D. The shaded region indicates the site of the mutation in the mutant sequences.

FIG. 1B depicts the nucleotide (SEQ ID NO: 14) and amino acid (SEQ ID NO: 15) sequences of the wild-type (WT) AHASL1B and nucleotide (SEQ ID NO: 16) and amino acid (SEQ ID NO: 17) sequences of the mutant (MUT) AHASL1B. The shaded region indicates the site of the mutation in the mutant sequences.

FIG. 1C depicts the nucleotide (SEQ ID NO: 18) and amino acid (SEQ ID NO: 19) sequences of the wild-type (WT) AHASL1A and nucleotide (SEQ ID NO: 20) and amino acid (SEQ ID NO: 21) sequences of the mutant (MUT) AHASL1A. The shaded region indicates the site of the mutation in the mutant sequences.

FIG. 6 is a table of percent nucleotide sequence identities from pairwise comparisons of the wheat AHASL gene coding sequences. Hexaploid L1D, Hexaploid L1B, and Hexaploid L1A denote the AHASL1D, AHASL1B, and AHASL1A genes, respectively, from *Triticum aestivum*. Tetraploid L1B, and Tetraploid L1A denote the AHASL1B and AHASL1A genes, respectively, from *T. Turgidum* ssp. *durum*.

SEQUENCE LISTING

Figure 2:
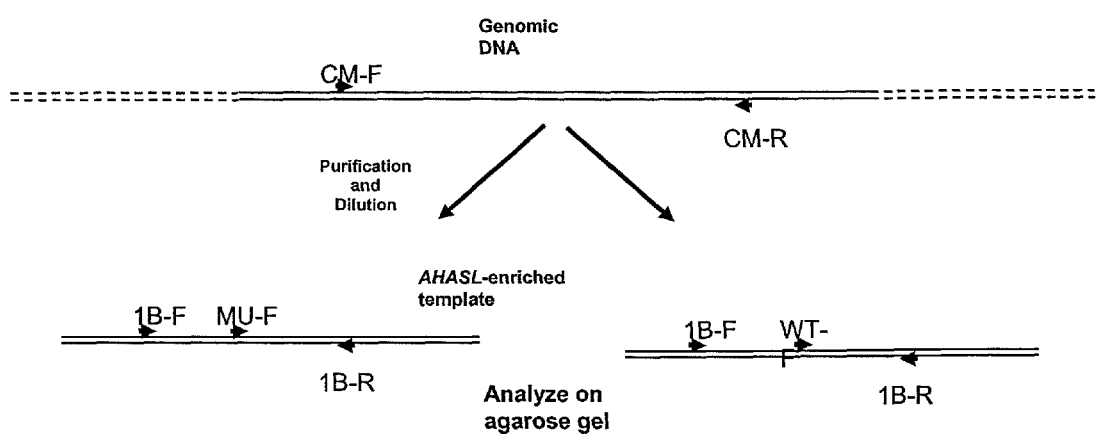
FIG. 2 is a schematic representation of one embodiment of the invention.

The nucleic acid and amino acid sequences listed in the accompanying sequence listing are shown using standard letter abbreviations for nucleotide bases, and three-letter code for amino acids. The nucleic acid sequences follow the standard convention of beginning at the 5' end of the sequence and proceeding forward (i.e., from left to right in each line) to the 3' end. Only one strand of each nucleic acid sequence is shown, but the complementary strand is understood to be included by any reference to the displayed strand. The amino acid sequences follow the standard convention of beginning at the amino terminus of the sequence and proceeding forward (i.e., from left to right in each line) to the carboxy terminus.

SEQ ID NO: 1 sets forth the nucleotide sequence of the forward AHASL primer, which is also referred to herein as CM-F.

SEQ ID NO: 2 sets forth the nucleotide sequence of the reverse AHASL primer, which is also referred to herein as CM-R.

SEQ ID NO: 3 sets forth the nucleotide sequence of the mutant-allele-specific primer, which is also referred to herein as MU-F.

SEQ ID NO: 4 sets forth the nucleotide sequence of the wild-type-allele-specific primer, which is also referred to herein as WT-F.

SEQ ID NO: 5 sets forth the nucleotide sequence of a forward AHASL-gene-specific primer, which is also referred to herein as 1A,D-F.

SEQ ID NO: 6 sets forth the nucleotide sequence of a forward AHASL-gene-specific primer, which is also referred to herein as 1B-F.

SEQ ID NO: 7 sets forth the nucleotide sequence of a reverse AHASL-gene-specific primer, which is also referred to herein as 1D-R.

SEQ ID NO: 8 sets forth the nucleotide sequence of a reverse AHASL-gene-specific primer, which is also referred to herein as 1B-R.

SEQ ID NO: 9 sets forth the nucleotide sequence of a reverse AHASL-gene-specific primer, which is also referred to herein as 1A-R.

SEQ ID NO: 10 sets forth the nucleotide sequence of a portion of the wild-type allele of AHASL1D that is depicted in FIG. 1A.

SEQ ID NO: 11 sets forth the amino acid sequence encoded by the portion of the nucleotide sequence of the wild-type allele of AHASL1D that is depicted in FIG. 1A SEQ ID NO: 12 sets forth the nucleotide sequence of a portion of the mutant allele of AHASL1D that is depicted in FIG. 1A.

SEQ ID NO: 13 sets forth the amino acid sequence encoded by the portion of the nucleotide sequence of the wild-type allele of AHASL1D that is depicted in FIG. 1A.

SEQ ID NO: 14 sets forth the nucleotide sequence of a portion of the wild-type allele of AHASL1B that is depicted in FIG. 1B.

SEQ ID NO: 15 sets forth the amino acid sequence encoded by the portion of the nucleotide sequence of the wild-type allele of AHASL1B that is depicted in FIG. 1B.

SEQ ID NO: 16 sets forth the nucleotide sequence of a portion of the mutant allele of AHASL1B that is depicted in FIG. 1B.

SEQ ID NO: 17 sets forth the amino acid sequence encoded by the portion of the nucleotide sequence of the wild-type allele of AHASL1B that is depicted in FIG. 1B.

SEQ ID NO: 18 sets forth the nucleotide sequence of a portion of the wild-type allele of AHASL1A that is depicted in FIG. 1C.

SEQ ID NO: 19 sets forth the amino acid sequence encoded by the portion of the nucleotide sequence of the wild-type allele of AHASL1A that is depicted in FIG. 1C.

SEQ ID NO: 20 sets forth the nucleotide sequence of a portion of the mutant allele of AHASL1A that is depicted in FIG. 1C.

SEQ ID NO: 21 sets forth the amino acid sequence encoded by the portion of the nucleotide sequence of the wild-type allele of AHASL1A that is depicted in FIG. 1C.

Figure 3:
FIG. 3 is a partial alignment of the three wheat AHASL cDNA sequences (AHASL1B, SEQ ID NO: 22; AHASL1D, SEQ ID NO: 23; AHASL1A, SEQ ID NO: 24) with the forward (CM-F, SEQ ID NO: 1) and reverse (CM-R, SEQ ID NO: 2) AHASL primers (shaded). The reverse primer, CM-R, is shown in the 3'-to-5' orientation in FIG. 3.

SEQ ID NO: 22 is the portion of the AHASL1B nucleotide sequence that is shown in FIG. 3.

SEQ ID NO: 23 is the portion of the AHASL1D nucleotide sequence that is shown in FIG. 3.

SEQ ID NO: 24 is the portion of the AHASL1A nucleotide sequence that is shown in FIG. 3.

Figure 4:
FIG. 4 is a partial alignment of the three wheat AHASL cDNA sequences (AHASL1B, SEQ ID NO: 25; AHASL1D, SEQ ID NO: 26; AHASL1A, SEQ ID NO: 27) with the wild-type-allele specific (WT-F, SEQ ID NO: 4), mutant-allele-specific (MU-F, SEQ ID NO: 3), forward AHASL-gene-specific (1AD-F, SEQ ID NO: 5: 1B-F, SEQ ID NO: 6) and reverse (1B-R, SEQ ID NO: 8; 1D-R, SEQ ID NO: 7; 1A-R, SEQ ID NO: 9) AHASL-gene-specific primers. The forward AHASL-gene-specific primers are shown in light shading. The reverse AHASL-gene-specific primers are shown in dark shading. The wild-type-allele specific and mutant-allele-specific primers are in italics and boldface type, respectively. The reverse primers, 1AD-R, 1B-R and 1A-R, are shown in the 3'-to-5' orientation in FIG. 4.

SEQ ID NO: 25 is the portion of the AHASL1B nucleotide sequence that is shown in FIG. 4.

SEQ ID NO: 26 is the portion of the AHASL1D nucleotide sequence that is shown in FIG. 4.

SEQ ID NO: 27 is the portion of the AHASL1A nucleotide sequence that is shown in FIG. 4.

DETAILED DESCRIPTION OF THE INVENTION

The invention is directed to rapid methods for analyzing the genomes of plants, particularly for analyzing the AHASL genes therein. The methods of the invention find particular use in analyzing the AHASL genes of plants with multiple AHASL genes such as, for example, bread wheat, *Triticum aestivum* L., and durum wheat, T. *Turgidum* ssp. *durum*. T. *aestivum* comprises in its hexaploid genome three highly similar, but distinct, AHASL genes, designated as AHASL1D, AHASL1B, and AHASL1A. In contrast, *T. turgidum* ssp. *durum* comprises in its tetraploid genome two highly similar, but distinct, AHASL genes, designated as AHASL1B, and AHASL1A gene. While not identical, AHASL1B and AHASL1A of *T. aestivum* are closely related to AHASL1B and AHASL1A of *T. turgidum* ssp. *durum* as is apparent from sequence alignments and calculations of percentage sequence identity. FIG. 6 provides nucleotide sequence identities from pairwise comparisons of the AHASL gene coding sequences of *T. aestivum* and *T. turgidum* ssp. *durum*.

The methods of the invention involve determining whether a mutant allele is present at one or more of the AHASL genes in the genome of a plant. The mutant alleles comprise nucleotide sequences that encode imidazolinone-tolerant AHASL proteins comprising the S653(At)N substitution. The methods further involve determining whether there is present at one or more of the AHASL genes a wild-type AHASL allele. In fact, the methods of the invention allow for the determination of the zygosity of each of the AHASL genes in a plant. For example, the methods of the invention can be used to rapidly determine—for each of the three AHASL genes in a wheat plant (or two AHASL genes in the case of durum wheat)—whether a wheat plant is homozygous for the mutant AHASL allele, heterozygous, or homozygous for the wild-type allele. Thus, the methods of the invention find use in breeding programs for the production of imidazolinone-tolerant wheat plants having one, two, three, four, five, or six mutant AHASL alleles in their genomes.

The following terms used herein are defined below.

A "primer" is a single-stranded oligonucleotide, having a 3' end and a 5' end, that is capable of annealing to an annealing site on a target DNA strand, and the primer serves as an initiation point for DNA synthesis by a DNA polymerase, particularly in a PCR amplification. Such a primer may or may not be fully complementary to its annealing site on the target DNA An "annealing" site on a strand of a target DNA is the site to which a primer is capable of annealing in the methods of the present invention.

Generally for the amplification of a fragment of a gene by PCR, a pair of primers that anneal to opposite strands of a double-stranded DNA molecule are employed. By standard convention, the "forward primer" anneals to the non-coding strand of the gene and the "reverse primer" primer anneals to the coding strand.

A "nested primer" is a primer that has an annealing site that lies between a region of DNA that is amplified by a particular pair of forward and reverse primers.

A "nested PCR" is amplification of a smaller fragment that is a portion of a larger fragment that was or is amplified by PCR. Generally, a first PCR is conducted with a particular pair of forward and reverse primers to produce a first fragment. Then a second PCR is conducted with a nested forward and a nested reverse primer, using the first fragment as a template such that a second fragment is produced. However, in certain embodiments of the invention a forward primer, a reverse primer, and a nested primer are used in the same PCR amplification. The forward primer and the nested primer anneal to the same strand of DNA and amplification of two fragments can occur during PCR: a larger fragment resulting from amplification of the region of the DNA template between the annealing sites of the forward primer and the reverse primer and a smaller fragment resulting from amplification of the region of the DNA template between the annealing sites of the nested primer and the reverse primer.

Throughout the specification, the terms "mutant allele," "mutant AHASL allele," or "mutant AHASL gene." Unless indicated otherwise herein, these terms refer to a polynucleotide that encodes an imidazolinone-tolerant AHASL protein comprising the S653(At)N substitution. This amino acid substitution is a result of a point mutation from G to A in the position that corresponds to nucleotide 1958 of the *Arabidopsis* AHASL nucleotide sequence set forth in EMBL Accession No. X51514, which is herein incorporated by reference. See, Sathasivan et al. (1990) *Nucl. Acids Res.* 18:2188; herein incorporated by reference.

In contrast, unless indicated otherwise, the terms "wild-type allele," "wild-type AHASL allele," or "wild-type AHASL gene" allele refer to a polynucleotide that encodes an AHASL protein that lacks the S653(At)N substitution. Such a "wild-type allele," "wild-type AHASL allele," or "wild-type AHASL gene" may, or may not, comprise mutations, other than the mutation that causes the S653(At)N substitution.

The invention involves the use of a number of primers for PCR amplification. These primers are described in detail below.

A "mutant-allele-specific primer" is a primer that can be used in the methods of the invention for the PCR amplification of a fragment of a mutant AHASL allele but allows relatively little or no amplification of a wild-type AHASL allele or portion thereof.

A "wild-type-allele-specific primer" is a primer that can be used in the methods of the invention for the PCR amplification of a fragment of a wild-type AHASL allele but allows relatively little or no amplification of a mutant AHASL allele or portion thereof.

A "forward AHASL-gene-specific primer" of the invention and a "reverse AHASL-gene-specific primer" of the invention are used as a primer pair in the amplification of a fragment of a particular AHASL gene, such as, for example, AHASL1D, AHASL1B, and AHASL1A of *T. aestivum* and AHASL1B, and AHASL1A of *T. turgidum* ssp. *durum*. The forward AHASL-gene-specific primer of the invention and the reverse AHASL-gene-specific primer of the invention include any pair of primers that can be used to produce a gene-specific amplification product, or fragment, that includes the site of the SNP that gives rise to the mutant AHASL allele. For example, the primer pair of SEQ ID NO: 6 (forward AHASL1B specific primer) and SEQ ID NO: 8 (reverse AHASL1B), when used in the methods of the present invention, is capable of specifically amplifying a fragment of wheat AHASL1B, but not a fragment of either wheat AHASL1D or AHASL1A. Thus, the invention does not depend on a particular forward AHASL-gene-specific primer or a reverse AHASL-gene-specific primer." Rather, a primer pair consisting of a particular forward AHASL-gene-specific primer and a particular reverse AHASL-gene-specific primer is capable of amplifying a fragment of only one specific AHASL gene from a plant. Those of ordinary skill in the art will recognize that numerous forward and reverse AHASL-gene-specific primers can be designed for use in the methods of the present invention. The methods of the present invention encompass the use of all such forward and reverse AHASL-gene-specific primers.

In addition, a reverse AHASL-gene-specific primer of the invention, when used in a PCR amplification together with either the wild-type-allele-specific primer of the invention or the mutant-allele-specific primer of invention, is capable of amplifying a fragment of only one specific AHASL gene from a plant. For example, the primer pair of SEQ ID NO: 3 (mutant-allele-specific primer) and SEQ ID NO: 8 (reverse AHASL1B), when used in the methods of the present invention, is capable of specifically amplifying a fragment of the wheat AHASL1B gene, but not a fragment of the wheat AHASL1D or AHASL1A genes. Similarly, the primer pair of SEQ ID NO: 4 (wild-type-allele-specific primer) and SEQ ID NO: 8 (reverse AHASL1B), when used in the methods of the present invention, is capable of specifically amplifying a fragment of the wheat AHASL1B gene, but not a fragment of the wheat AHASL1D or AHASL1A genes.

For the amplification of a fragment of the AHASL1D gene of *T. aestivum*, a preferred forward AHASL-gene-specific primer has the nucleotide sequence set forth in SEQ ID NO: 5 and a reverse AHASL-gene-specific primer has the nucleotide sequence set forth in SEQ ID NO: 7.

For the amplification of a fragment of the AHASL1B genes of both *T. aestivum* and *T. turgidum* ssp. *durum*, a preferred forward AHASL-gene-specific primer has the nucleotide sequence set forth in SEQ ID NO: 6 and a reverse AHASL-gene-specific primer has the nucleotide sequence set forth in SEQ ID NO: 8.

For the amplification of a fragment of the AHASL1A genes of both *T. aestivum* and *T. turgidum* ssp. *durum*, a preferred forward AHASL-gene-specific primer has the nucleotide sequence set forth in SEQ ID NO: 5 and a reverse AHASL-gene-specific primer has the nucleotide sequence set forth in SEQ ID NO: 9.

For plants with more than one AHASL gene in their genomes, a "forward AHASL primer" of the invention and "reverse AHASL primer" of the invention" are used as a primer pair in the amplification of a fragment of each of the AHASL genes of a plant. That is, the pair of the forward AHASL primer and the reverse AHASL primer are designed to not discriminate between the different AHASL genes in a in a plant and thus, are generic AHASL primers for a plant species of interest. The amplification product or fragment that results from a PCR amplification of genomic DNA with the forward AHASL primer and the reverse AHASL primer includes the annealing sites of the forward and reverse AHASL-gene-specific primers described above.

The particular PCR amplification of the invention that involves the use of the forward AHASL primer and the reverse AHASL primer is referred to herein as the pre-amplification step. In certain embodiments of the invention, the pre-amplification step is employed to enrich the genomic DNA with fragments comprising AHASL genes for use in subsequent PCR amplifications of the invention. The product of the pre-amplification step is referred to herein as pre-amplified DNA.

Unless otherwise indicated herein, "polymerase" refers to a DNA polymerase, particularly a DNA polymerase that is suitable for use in one or more of the PCR amplifications of the present invention.

The present invention involves three aspects. The first aspect of the invention comprises a first PCR amplification of genomic DNA or pre-amplified DNA, to detect a mutant AHASL allele from a plant. The second aspect includes the first PCR amplification of the first aspect and adds a second PCR amplification of a genomic DNA, or the pre-amplified DNA, to detect the wild-type AHASL allele from a plant. The third aspect includes the first PCR amplification of the first aspect, the second PCR amplification of the second aspect, and adds a third PCR amplification to amplify the AHASL genes or fragments thereof using genomic DNA as the template source. This third PCR amplification, also referred to herein as pre-amplification, is performed prior to the first and second PCR amplifications. The product of the third PCR amplification, also referred to herein as pre-amplified DNA, is used as the DNA template source for the first and second PCR amplifications.

The first aspect of the invention is a method for detecting a mutant allele of an AHASL gene that confers tolerance to imidazolinone herbicides on a plant plant. The mutant allele of the invention encodes an imidazolinone-tolerant AHASL protein comprising the S653(At)N substitution. The method is directed to determining whether there is a mutant AHASL allele present at a specific AHASL gene of a plant. In an embodiment of the invention, the plant is *T. aestivum* or *T. turgidum* ssp. *durum* and the AHASL gene is selected from the group consisting of AHASL1D, AHASL1B, and AHASL1A of *T. aestivum* and the AHASL1B and AHASL1A of *T. turgidum* ssp. *durum*.

An important feature of the first aspect of the invention is the discovery that the mutant-allele-specific primer having the nucleotide sequence set forth in SEQ ID NO: 3, together with a reverse AHASL-gene specific primer of the invention, can be used to selectively amplify by PCR a portion of the mutant AHASL allele, while allowing relatively little or no amplification of the corresponding region of the wild-type AHASL allele. Typically, primers that are developed for PCR methods for distinguishing between two alleles that vary by a single nucleotide substitution are designed such that the primers reflect the same polymorphism at their 3' end. The basis for this primer design is the premise that oligonucleotides with a mismatched 3' end-residue will not function as primers in PCR under the appropriate conditions (Newton et al. (1989) *Nucl. Acids Res.* 17:2503-2516; and Wu et al. (1989) *Proc. Natl. Acad. Sci. USA* 86: 2757-2760). In contrast, the nucleotide at the 3' end of the mutant allele-specific primer mismatches both the mutant and wild-type alleles at the site of the SNP. Primers that were designed to have a 3' end nucleotide that mismatches the wild-type wheat AHASL allele but matches the mutant allele at the site of SNP were unexpectedly found to allow the amplification of the both the mutant and wild-type alleles. Therefore, other primer designs were tested. The surprising result was that a primer such as the mutant-allele-specific primer having the nucleotide sequences set forth SEQ ID NO: 3, which has a 3' end residue that mismatches both the wild-type and mutant alleles at the site of the SNP, was capable of allowing the amplification of the mutant wheat AHASL allele while allowing little or no amplification of the wild-type wheat AHASL allele.

The mutant-allele-specific primers of the invention are designed to anneal to the non-coding strand of at least one AHASL gene of interest in the region of the G-to-A point mutation that gives to the S653(At)N substitution in an AHASL protein. In particular, the mutant-allele-specific primers of the invention comprise a nucleotide sequence with a 5' end and a 3' end, wherein the nucleotide sequence corresponds to the coding strand of an AHASL gene, the 3' end nucleotide corresponds to the site of the G-to-A point mutation, and the 3' end nucleotide is cytidine. Thus, such a primer comprises at least one nucleotide that is not identical to the corresponding region of the coding strand of the AHASL gene of interest.

For analyzing the AHASL genes of wheat, the invention provides a mutant allele-specific primer that is capable annealing to the mutant AHASL alleles for each of the wheat AHASL genes. The region of DNA in the vicinity of the SNP that results in the mutant AHASL allele of the invention is nearly identical across the three *T. aestivum* AHASL genes and the two *T. turgidum* ssp. *durum* AHASL genes. Thus, the mutant-allele-specific primers of the invention are capable annealing to the mutant AHASL alleles for each of the three *T. aestivum* AHASL genes and the two *T. turgidum* ssp. *durum* AHASL genes. Such mutant-allele-specific primers of the invention comprise a nucleotide sequence with a 5' end and a 3' end, wherein the nucleotide sequence is capable of annealing to the complement of nucleotides 3 to 23 of SEQ ID NO: 12, has a cytidine at the 3' end, and is capable of annealing to a region of an AHASL gene that is nested between the annealing sites of the forward and reverse AHASL-genespecific primers of the invention. A preferred mutant-allele-specific primer of the invention has the nucleotide sequence set forth in SEQ ID NO: 3.

The first PCR amplification comprises three primers, the mutant-allele-specific primer and a pair of primers designed to selectively amplify a specific AHASL gene in a plant. The primer pair comprises a forward AHASL-gene-specific primer and a reverse AHASL-gene-specific primer that are designed for the selective PCR amplification of a fragment of only one specific AHASL gene from a plant.

Using the methods of the invention, there are two results from the first PCR amplification of genomic DNA from a plant. The results can be detected by, for example, agarose gel electrophoresis of the PCR products followed by ethidium-bromide staining of the DNA in the gel and visualization in the presence of UV light. If the specific AHASL gene comprises at least one mutant allele, the first PCR amplification produces two DNA fragments, a larger fragment resulting from amplification of the region of the AHASL gene bounded by the annealing sites of the forward and reverse AHASL-gene-specific primers and a smaller fragment resulting from amplification of the region of the AHASL gene bounded by the annealing sites of the mutant-allele-specific primer and the reverse AHASL-gene-specific primer. If, however, the specific AHASL gene does not comprise at least one mutant allele, then the first PCR amplification produces only the larger fragment.

The second aspect of the invention is method for analysis of an AHASL gene. The invention is directed to determining whether there is a wild-type allele, a mutant allele, or both present at a specific AHASL gene of a plant. In an embodiment of the invention, the plant is *T. aestivum* or *T. turgidum* ssp. *durum* and the AHASL gene is selected from the group consisting of AHASL1D, AHASL1B, and AHASL1A of *T. aestivum* and the AHASL1B and AHASL1A of *T. turgidum* ssp. *durum*.

The second aspect of the invention adds to the first PCR amplification of the first aspect a second PCR amplification involving the amplification of a portion of a wild-type AHASL allele. The second PCR involves the wild-type-allele-specific primer. The second aspect of the invention involves the use of a wild-type-allele-specific primer of the invention. A wild-type-allele-specific primer of the invention, together with a reverse AHASL-gene-specific primer of the invention, can be used to selectively amplify by PCR a portion of the wild-type AHASL allele, while allowing relatively little or no amplification of the corresponding region of a mutant AHASL allele.

The wild-type-allele-specific primers of the invention are designed to anneal to the non-coding strand of at least one AHASL gene of interest in the region of the G-to-A point mutation that gives to the S653(At)N substitution in an AHASL protein. The wild-type-allele-specific primers comprise a nucleotide sequence with a 5' end and a 3' end, wherein the nucleotide sequence corresponds to the coding strand of an AHASL gene, the 3' end nucleotide corresponds to the site of the G-to-A point mutation, and the 3' end nucleotide is guanosine.

For analyzing the AHASL genes of wheat, the invention provides a wild-type allele-specific primer that is capable annealing to the wild-type AHASL alleles for each of the wheat AHASL genes. Similar to the mutant-allele-specific primers of the invention, the wild-type-allele-specific primers of the invention are not designed to distinguish among the individual wheat AHASL genes, and thus are capable annealing to the wild-type AHASL alleles for each of the three *T. aestivum* AHASL genes and the two *T. turgidum* ssp. *durum*

AHASL genes. Such wild-type-allele-specific primers of the invention comprise a nucleotide sequence with a 5' end and a 3' end, wherein the nucleotide sequence is capable of annealing to the complement of nucleotides 4 to 23 of SEQ ID NO: 10, has a guanosine at the 3' end, and is capable of annealing to a region of an AHASL gene that is nested between the annealing sites of the forward and reverse AHASL-gene-specific primers of the invention. A preferred wild-type-allele-specific primer of the invention has the nucleotide sequence set forth in SEQ ID NO: 4.

Typically, in the method of the second aspect, the genomic DNA used in the second PCR amplification is from the same plant as the genomic DNA used in the first PCR amplification. Preferably, the first and second PCR amplifications each involve the use of a portion of the same isolated genomic DNA sample and that such a genomic DNA sample can be subjected to a pre-amplification step as described herein to enrich the genomic DNA sample for AHASL gene sequences or fragments thereof. It is recognized, however, that the methods of the second aspect can involve the use of genomic DNA isolated from a first plant for the first PCR amplification and the use of genomic DNA isolated from a second wheat plant for the second PCR amplification, if the first and second plants are known to be genetically identical.

The second PCR amplification comprises three primers, the wild-type-allele-specific primer and a pair of primers designed to selectively amplify a specific AHASL gene in a plant. The primer pair comprises a forward AHASL-gene-specific primer and a reverse AHASL-gene-specific primer that are designed for the selective PCR amplification of a fragment of only one specific AHASL gene from a plant. The specific AHASL gene is the same AHASL gene as in the first PCR amplification. Preferably, the forward AHASL-gene-specific primer and the reverse AHASL-gene-specific primer for the second PCR amplification are identical to those used in the first PCR amplification. The methods of the invention, however, do not depend on the use of identical forward and reverse AHASL-gene-specific primer pairs in both the first and second PCR amplifications.

There are two results from the second PCR amplification of genomic DNA from a plant. The products of the second PCR amplification can be detected as described above for the detection of the products of the first PCR amplification or by any other method for detecting PCR products known in the art. If the specific AHASL gene comprises at least one wild-type AHASL allele, the second PCR amplification produces two DNA fragments, a larger fragment resulting from amplification of the region of the AHASL gene bounded by the annealing sites of the forward and reverse AHASL-gene-specific primers and a smaller fragment resulting from amplification of the region of the AHASL gene bounded by the annealing sites of the wild-type-allele-specific primer and the reverse AHASL-gene-specific primer. If, however, the specific AHASL gene does not comprise at least one wild-type AHASL allele, then the first PCR amplification produces only the larger fragment.

In both the first and second PCR amplifications, the larger fragment is produced whether or not, the smaller fragment is produced. Thus, the larger fragment serves as an internal control to indicate that there was a successful first or second PCR amplification. If a first and/or second PCR amplification fails to produce the larger fragment, then that PCR was unsuccessful and should be repeated.

The methods of the invention do not depend on performing the first and second PCR amplifications simultaneously and in the same thermocycler. Typically, however, the first and second PCR amplifications of the genomic DNA of a particular plant will be performed simultaneously in the same thermocycler. Also, if the analysis of two, three, or more AHASL genes of a plant is desired, the first and second PCR amplifications for each of the AHASL genes can be conducted simultaneously in the same thermocycler. Furthermore, if the analysis of the one or more AHASL genes of two or more plants is desired, the first and second PCR amplifications for each of the wheat plants can be performed simultaneously in the same thermocycler, depending on the capacity of the thermocycler. In an embodiment of the invention that is suited for the high-throughput analysis of multiple wheat plants, the first and second PCR amplifications are preformed in a thermocycler that accommodates a standard 384-well PCR plates. The use of such a thermocycler and PCR plate allows for the simultaneous performance of the first and second PCR amplifications for each of the three AHASL genes for up to 64 wheat plants.

The third aspect of the invention comprises the method of the second aspect of the invention and further comprises a pre-amplification step. The pre-amplification step involves a third PCR amplification that is performed prior to the first and second PCR amplifications. The pre-amplification allows the amplification of at least a fragment of each of the AHASL genes so as to enrich the genomic DNA sample for the AHASL genes, or fragments thereof. For example, in the case of wheat, the pre-amplification allows the amplification of at least a fragment of each of the three AHASL genes (or two in the case of durum wheat) so as to enrich the genomic DNA sample for the three AHASL genes, or fragments thereof. By enriching the genomic DNA sample for the AHASL genes, or fragments thereof, the quantity and quality of the products produced by the first and second PCR amplifications can be improved. While the methods of the invention do not depend on any particular mechanism, it is presumed that the improvement in the first and second PCR amplifications from the pre-amplification step is the result of an increased amount of AHASL templates in the pre-amplified genomic DNA.

The pre-amplification step involves the use of a forward AHASL primer and a reverse AHASL primer for PCR amplification. For a plant that has two or more AHASL genes in its genome, the forward AHASL primer and the reverse AHASL primer are generic AHASL primers that do not discriminate between the two or more AHASL genes in the plant. Any pair of forward and reverse AHASL primers can be employed in a method of the invention, wherein such a pair of primers is capable of amplifying by PCR a fragment from the same region of all of the AHASL genes in a plant and such a fragment includes the annealing sites of the forward and reverse AHASL-gene-specific primers described above.

If desired, the products of the pre-amplification step can be subjected to exonuclease digestion by any method known in the art to reduce or eliminate single-stranded DNA, particularly any forward and/or reverse AHASL primers that remain after the pre-amplification is completed. Such an exonuclease digestion of the pre-amplified genomic DNA, prior to the first and second PCR amplifications, can further improve the first and second PCR amplifications. For example, Exonuclease T (RNase T), S1 nuclease from *Aspergillus oryzae*, mung bean nuclease, or Exonuclease I *Escherichia coli* may be used to remove the single-stranded DNA from the pre-amplification products. Alternatively, the products of the pre-amplification step can be purified to remove the forward and reverse AHASL primers. Any method may be used for this purification step, including, but not limited to, commercially available PCR purification methods such as the Wizard MagneSil PCR Cleanup System (Promega Corp., Madison, Wis., USA).

In one embodiment, the methods of the invention find use in determining the zygosity of an individual wheat plant at one, two, or three of the specific AHASL genes therein, namely AHASL1D, AHASL1B, and AHASL1A. In particular, the methods of second and third aspect can be used to determine zygosity at one or more of AHASL1D, AHASL1B, and AHASL1A. This is accomplished by conducting the methods of the second and third aspects one, two, or three times, each time using a different pair of forward and reverse AHASL-gene-specific primers for the first and second PCR amplifications, wherein each primer pair is designed to selectively amplify a fragment of one of the three wheat AHASL genes.

In a preferred embodiment of the invention, the zygosity of single wheat plant is determined for AHASL1D, AHASL1B, and AHASL1A. Genomic DNA from a wheat plant is pre-amplified using a forward AHASL primer having the nucleotides sequence set forth in SEQ ID NO: 1 and a reverse AHASL primer having the nucleotides sequence set forth in SEQ ID NO: 2. The pre-amplified genomic DNA is digested with Exonuclease I. Three pairs of first and second PCR amplifications are then conducted. For the first pair of PCR amplifications, the forward AHASL-gene-specific primer and reverse AHAS-gene-specific primers are designed to selectively amplify AHASL1D and have the nucleotide sequences set forth in SEQ ID NO: 5 and 7, respectively. For the second pair of PCR amplifications, the forward AHASL-gene-specific primer and reverse AHAS-gene-specific primers are designed to selectively amplify AHASL1B and have the nucleotide sequences set forth in SEQ ID NO: 6 and 8, respectively. For the third pair of PCR amplifications, the forward AHASL-gene-specific primer and reverse AHAS-gene-specific primers are designed to selectively amplify AHASL1A and have the nucleotide sequences set forth in SEQ ID NO: 5 and 9, respectively. In each instance, the mutant-allele-specific primer is SEQ ID NO: 3, and the wild-type-allele-specific primer is SEQ ID NO: 4. The products of the six PCR amplifications are then detected by agarose gel electrophoresis and ethidium-bromide staining.

The present invention also provides kits for performing the methods of the invention as described herein. Such kits comprise at least one forward AHASL-gene-specific primer, at least one reverse AHASL-gene-specific primer, a mutant-allele-specific primer, at least one polymerase enzyme capable of catalyzing the PCR amplification of a first fragment of a wheat AHASL gene and a second fragment of a wheat AHASL gene, wherein the first fragment is between the annealing site of the forward AHASL-gene-specific primer and the annealing site of the reverse AHASL-gene-specific primer and the second fragment is between the annealing site of the mutant-allele-specific primer and the annealing site of the reverse AHASL-gene-specific primer. The kits of the invention can further comprise at least one additional component selected from the group consisting of wild-type-allele-specific primer, a forward AHASL primer, a reverse AHASL primer, an additional polymerase enzyme, a concentrated buffer solution, a solution of $MgCl_2$, deoxyribonucleotide triphosphates, and Exonuclease I.

The methods of the invention involve the use of PCR for amplifying DNA. Oligonucleotide primers can be designed for use in PCR reactions to amplify corresponding DNA sequences from genomic DNA or cDNA extracted from any organism of interest. Methods for designing PCR primers are generally known in the art and are disclosed in Sambrook et al. (1989) *Molecular Cloning: A Laboratory Manual* (2d ed., Cold Spring Harbor Laboratory Press, Plainview, N.Y.); herein incorporated by reference. See also, Innis et al., eds.

(1990) *PCR Protocols: A Guide to Methods and Applications* (Academic Press, New York); Innis and Gelfand, eds. (1995) *PCR Strategies* (Academic Press, New York); Innis and Gelfand, eds. (1999) *PCR Methods Manual* (Academic Press, New York); Dietmaier et al., eds. (2002) *Rapid Cycle Real Time PCR—Methods and Applications*, (Springer Verlag, New York); Theophilus and Raphley, eds. (2002) *PCR Mutation Detection Protocols* (Humana Press, New York); and Bartlett and Stirling, eds. (2003) *PCR Protocols* (Humana Press, New York); all of which are herein incorporated by reference. Other known methods of PCR that can be used in the methods of the invention include, but are not limited to, methods using paired primers, nested primers, single specific primers, degenerate primers, gene-specific primers, mixed DNA/RNA primers, vector-specific primers, partially-mismatched primers, and the like.

While the invention does not depend on PCR primers of any particularly number of nucleotides, it is recognized that the portion of a PCR primer that anneals to its complementary target on the template DNA will generally be between about 10 and 50 contiguous nucleotides, preferably 10, 11, 12, 13, 14, 15, 16, 17, 18, 19, 20, 21, 22, 23, 24, 25, 26, 27, 28, 29, 30, or more contiguous nucleotides. However, a PCR primer of the invention can further comprise on its 5' end additional nucleotides that are not intended to anneal to the target such as, for example, a DNA sequence comprising one or more restriction enzyme recognition sites.

The methods of the invention involve the use of DNA polymerases for PCR amplification of DNA. Any DNA polymerase known in the art that is capable of amplifying a target DNA by PCR may be used in the methods of the invention. The methods of the invention do not depend on a particular DNA polymerase for PCR amplification of DNA, only that such polymerases are capable of amplifying one or more of the plant AHASL genes or fragments thereof. Preferably, the DNA polymerases of the invention are thermostable DNA polymerases, including but not limited to: Taq polymerases; Pfu polymerases; themostable DNA polymerases from *Thermococcus gorgonarious* which are also known as Tgo DNA polymerases; thermostable DNA polymerases from *Thermococcus litoralis* such as, for example, those that are known as Vent® DNA polymerases (Perler, F. et al. (1992) *Proc. Natl. Acad. Sci. USA* 89, 5577), thermostable DNA polymerases from *Pyrococcus* species GB-D such as, for example, those that are known as Deep Vent® DNA polymerases (Xu, M. et al. (1993) *Cell* 75, 1371-1377); and modified versions and mixtures thereof.

In one embodiment of the invention, the PCR amplifications of the first and second aspects of the invention described above comprise "hot-start" PCR. Such "hot start" PCR involves methods that are known in art and is generally employed to reduce non-specific amplification products. Typically, "hot start" PCR methods involve combining the template DNA, primers, and other reaction components with the exception of the DNA polymerase, then holding the reaction mixture, for a period of time prior to introduction of the DNA polymerase, at a temperature above the threshold temperature for non-specific binding of the primers to the template, then adding DNA polymerase to the reaction mixture while the reaction mixture is maintained at a temperature above the threshold temperature.

Although the methods of the present invention do not depend on "hot start" PCR or a particular thermostable DNA polymerase, the preferred DNA polymerase for the PCR amplifications of the first and second aspects of the invention is HotStarTaq DNA Polymerase (Qiagen Inc., Valencia, Calif., USA). HotStar DNA polymerase is a modified form of Taq DNA polymerase that is supplied by the manufacturer in an inactive state that has no DNA polymerase activity at ambient temperatures. The inactivity at ambient temperatures prevents extension of nonspecifically annealed primers and primer-dimers formed at low temperatures during the setup of PCR reaction mixtures and while the tubes are heated to reach the initial denaturation temperature. HotStarTaq DNA Polymerase is activated by a 15-minute incubation at 95° C. which can be incorporated into any existing thermal-cycler program. Thus, HotStar DNA polymerase allows for hot start PCR without the need to physically separate the DNA polymerase from the other components of the reaction mixture during the time that reaction mixture is heated to a temperature above the threshold temperature.

In another embodiment of the invention, the PCR amplification of the third aspect of the invention, also referred to herein as the pre-amplification, comprises at least one proofreading DNA polymerase, which comprises a 3'-to-5' exonucleases activity. Such proofreading DNA polymerases include, but are not limited to Tgo DNA polymerases, Vent® DNA polymerases, and Deep Vent® DNA polymerases as described above. In a preferred embodiment of the invention, the pre-amplificaiton comprises the Expand High Fidelity PCR System (Roche Applied Science, Indianapolis, Ind., USA). The Expand High Fidelity PCR System comprises Taq DNA polymerase and a proofreading DNA polymerase, Tgo DNA polymerase, that minimizes mutations that may result from the inadvertent misincorporation of a non-complementary nucleotide. Such PCR-induced mutations could interfere with the PCR amplification of the first and second aspects of the invention as disclosed herein. Therefore, a high-fidelity amplification, such as that which can be obtained with a PCR amplification comprising a proofreading DNA polymerase, is desired for the pre-amplification.

The methods of the invention involve the amplification of a target DNA sequence by PCR. In certain embodiments of the invention, the target DNA sequence will amplified directly from a sample comprising genomic DNA isolated from at least one plant or part, organ, tissue, or cell thereof. Those of ordinary skill in the art will recognize that the amount or concentration of genomic DNA will depend on any number of factors including, but not limited to, the PCR conditions (e.g. annealing temperature, denaturation temperature, the number of cycles, primer concentrations, dNTP concentrations, and the like), the thermostable DNA polymerase, the sequence of the primers, and the sequence of the target. Typically, in the embodiments of the invention described herein, the concentration of genomic DNA is at least about 5 ng/µL to about 100 ng/µL.

In addition to PCR amplification, the methods of the invention can involve various techniques of molecular biology including, for example, DNA isolation, particularly genomic DNA isolation, digestion of DNA by restriction enzymes and nucleases, DNA ligation, DNA sequencing, agarose gel electrophoresis, detection of DNA by ethidium-bromide staining, and the like. Such techniques are generally known in the art and are disclosed, for example, in Sambrook et al. (1989) *Molecular Cloning: A Laboratory Manual* (2d ed., Cold Spring Harbor Laboratory Press, Plainview, N.Y.).

The methods of the invention involve the use of genomic DNA isolated from a plant. The methods of the invention do not depend on genomic DNA isolated by any particular method. Any method known in the art for isolating, or purifying, from a plant, genomic DNA, which can be used a source of template DNA for the PCR amplifications described above, can be employed in the methods of the invention. See, for example, Stein et al. ((2001) *Plant Breeding*, 12:354-356);

Clark, ed. ((1997) *Plant Molecular Biology—A Laboratory Manual*, Springer-Verlag, New York, pp. 3-15); Miller et al., ((1988) *Nucleic Acids Research*, 16:1215); all of which are herein incorporated by reference. Preferably, such methods for isolating plant genomic DNA are suited, or can be adapted by one of ordinary skill in the art, for the isolation of genomic DNA from relatively large numbers of tissue samples of plants. In an embodiment of the invention, genomic DNA is isolated from wheat plants using a DNeasy® kit according to the manufacturer's instructions (Qiagen Inc., Valencia, Calif., USA). In another embodiment, genomic DNA is isolated from wheat plants using a MagneSil® kit according to the manufacturer's instructions (Promega Corp., Madison, Wis., USA).

For the methods of the present invention, genomic DNA can be isolated from whole plants or any part, organ, tissue, or cell thereof. For example, genomic DNA can be isolated from seedlings, leaves, stems, roots, inflorescences, seeds, embryos, tillers, coleotiles, anthers, stigmas, cultured cells, and the like. Furthermore, the invention does not depend on the isolation of genomic DNA from plants or parts, organs, tissues, or cells thereof that are of any particular developmental stage. The methods can employ genomic DNA that is isolated from, for example, seedlings or mature plants, or any part, organ, tissue or cell thereof. Furthermore, the invention does not depend on plants that are grown under any particular conditions. The plants can be grown, for example, under field conditions, in a greenhouse, or a growth chamber, in culture, or even hydroponically in a greenhouse or growth chamber. Typically, the plants will be grown in conditions of light, temperature, nutrients, and moisture that favor the growth and development of the plants.

The methods of invention involve detecting the products of the PCR amplifications, particularly the first and second PCR amplifications. Typically, the PCR products are detected by first separating the products in a substrate on the basis of molecular weight and then detecting each of the separated PCR products in the substrate. In a preferred embodiment of the invention, the PCR products are detected by agarose gel electrophoresis of the PCR products followed by ethidium-bromide staining of the DNA in the gel and visualization in the gel by florescence in the presence of UV light. However, any detection method suitable for separating polynucleotides can be used to detect the PCR products of the invention including, but not limited to, gel electrophoresis, high performance liquid chromatography, capillary electrophoresis, and the like. Substrates for such methods include, for example, agarose, polyacrylamide, diethylaminoetyl cellulose, hydroxyalkyl cellulose, sepharose, polyoxyethylene, and the like. The PCR amplifications of the invention can involve the use of one or more primers that are labeled, for example, radioactively, or with a fluorescent dye, a luminescent label, a paramagnetic label, or any other label suitable for the detection of nucleic acids. When the PCR amplifications involve one or more of such a labeled primers, the detection step can include the detection of the radioactive, fluorescent, luminescent, paramagnetic, or other label by any methods known in the art for detecting such a label.

The methods of the invention as disclosed herein can be used to analyze the AHASL genes of any plant species of interest. Examples of plant species of interest include, but are not limited to, corn or maize (*Zea mays*), *Brassica* sp. (e.g., *B. napus*, *B. rapa*, *B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum, T. Turgidum* ssp. *durum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassaya (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers. Preferably, plants of the present invention are crop plants (for example, wheat, corn, rice, barley, oats, sugar beet, alfalfa, sunflower, *Brassica*, soybean, cotton, safflower, peanut, sorghum, millet, tobacco, etc.), more preferably grain plants (for example, wheat, corn, rice, barley, sorghum, rye, triticale, etc.), yet more preferably wheat plants.

The following examples are offered by way of illustration and not by way of limitation.

EXAMPLE 1

The AHASL Genes of Wheat

Three acetohydroxyacid synthase large subunit (AHASL) sequence variants were identified from sequencing of wheat cDNAs. The genes corresponding to these variants were mapped to their respective genome and chromosome arm (6L) and were named on the basis of the genome in which they reside (e.g., AHASL on genome A=AHASL1A). Nucleotide sequences for multiple varieties of *Triticum aestivum* AHASL1A, AHASL1B and AHASL1D transcripts were obtained. These sequences comprise the full coding sequences for the mature polypeptides. See, U.S. Application entitled "Polynucleotides Encoding Mature AHASL Proteins For Creating Imidazolinone-Tolerant Plants", filed concurrently herewith, herein incorporated in its entirety by reference.

A comparison of imidazolinone (IMI)-tolerant mutant varieties with wild-type progenitors revealed that the most common type of mutation was a G-to-A transition, which produces a serine (S) to asparagine (N) substitution in a position corresponding to S653 in the model taxon, *Arabidopsis thaliana* (Sathasivan et al. (1991) *Plant Physiol.* 97:1044-1050; Hattori et al. (1992) Mol. Gen. Genet. 232:167-173). The semi-dominant mutation, now termed S653 (At)N, is also found in other IMI-tolerant crops. See, for example, U.S. Pat. No. 5,731,180; and U.S. application Ser. No. 10/695,089, filed Oct. 28, 2003.

EXAMPLE 2

A Rapid Method for Distinguishing the Wheat AHASL Genes and Their Respective Alleles To facilitate the rapid identification of S653(At)N mutations in wheat, methods for allele-specific PCR assays for mutations in each of the three AHASL genes were developed. The IMI-tolerant varieties used for the assay development are set forth in Table 1.

TABLE 1

Wheat Lines Used for Assay Development

| Wheat Line | Mutated Gene | Old Designation |
|---|---|---|
| CV9804 | TaAHASL1D | ALS1 |
| G-208 | TaAHASL1B | ALS2 |
| K-42 | TaAHASL1A | ALS3 |
| Krichauff | None | NA |

From the nucleotide sequences of the mutant and wild-type wheat AHASL genes, a method involving a set of six allele-specific PCR assays for high-throughput genotyping of bread and durum wheat lines containing the S653(At)N mutation was developed.

The assays were designed as allele-specific PCR methods using a pair of primers, in which one primer is specific to the allele (mutant or wild type) and the second specific to gene (AHASL1D vs. AHASL1B vs. AHASL1A). Adding a second gene-specific primer upstream of the allele-specific primer added a further refinement in that each reaction now contained an internal control for DNA quantity/quality. Each reaction could now produce two products. The "diagnostic" band is the product of the allele-specific and gene-specific primer pair, while a higher molecular weight "control" band represents the product of both gene-specific primers. The presence of the control band in the absence of the diagnostic band indicates that the reaction was successful and the allele in question is not present in the sample. Finally, a preliminary DNA amplification step was added to increase the template quantity and purity in the allele-specific PCR step, thus ensuring consistent amplification from DNA samples of varied quantity and quality. See, FIG. 2 for a schematic overview of this embodiment of the invention.

An important aspect of the method is the development of the mutant allele-specific primer MU-F (SEQ ID NO: 3). Typically, primers that are developed for PCR methods for distinguishing between two alleles that vary by a single nucleotide substitution are designed such that the primers reflect the same polymorphism at their 3' end. The basis for this primer design is the premise that oligonucleotides with a mismatched 3' end-residue will not function as primers in PCR under the appropriate conditions (Newton et al. (1989) *Nucl. Acids Res.* 17:2503-2516; and Wu et al. (1989) *Proc. Natl. Acad. Sci. USA* 86: 2757-2760). In contrast, the nucleotide at the 3' end of the MU-F mismatches both the mutant and wild-type alleles at the site of the SNP. Primers that were designed to have a 3' end nucleotide that mismatches the wild-type allele but matches the mutant allele at the site of SNP were unexpectedly found to allow the amplification of the wild-type allele. Therefore, other primer designs were tested. The unexpected result was that a primer such as MU-F, which has a 3' end residue that mismatches both the wild-type and mutant alleles at the site of the SNP, could allow the amplification of the mutant allele but not the wild-type allele in the methods of the invention.

Although the MU-F primer is capable of annealing to a DNA sequence that is exactly complementary to MU-F, a mutant allele of a wheat AHASL that comprises such a DNA sequence is expected to be very rare and has not been detected in nature. Such a mutant allele would have a cytidine at the same nucleotide that is the site of the SNP that results in the S653(At)N mutation. Commonly, wheat plants having the S653(At)N mutation are produced by ethane methylsulfonate (EMS) mutagenesis. EMS generates primarily G•C-to-A•T transitions. The S653(At)N mutation results from such a G•C-to-A•T transition. See, FIGS. 1A, 1B, and 1C.

FIG. 2 is a schematic representation of one embodiment of the invention in which two PCR reactions are used to detect the S653(At)N mutation and determine the zygosity of AHASL1B. Any number of reactions (one to six) may be used depending on application. For example, if one is interested only in the presence of the S653(At)N mutation in only AHASL1A and AHASL1B, but not whether the mutations are homozygous, then only two reactions are required.

This gel-based PCR test consists of nested PCR with the first round consisting of a single reaction with common primers (CM-F, CM-R). A second round consisting of a single or multiple individual reactions, up to three (AHASL1A, AHASL1B, AHASL1D) for the mutant (IMI-tolerant) allele and one for the wild-type (susceptible) allele. Each of these second-round reactions contains three primers, the nested forward and reverse gene-specific primers (e.g. 1B-F, 1B-R) plus an allele-specific primer (i.e., WT-F or MU-F) with the mutated/wild-type base on its 3' primer end for amplification of the resistant/susceptible locus respectively. The larger PCR product (resulting from amplification between the forward and reverse gene-specific primers) is expected to be produced in all instances, and thus, this PCR product serves as a positive control for the PCR reaction (control band). The smaller PCR product (resulting from amplification between the allele-specific primer and reverse gene-specific primer) is an allele-specific PCR product (diagnostic band). For each PCR reaction, the smaller PCR product is expected to be produced only when the particular AHASL gene of interest comprises at least one AHASL allele that corresponds to the AHASL allele-specific primer (i.e., WT-F or MU-F) that was included in the PCR reaction mixture. The reaction products are separated on a 3.5% Agarose-1000 gel. Agarose-1000 is cross-linked agarose that can be obtained from Invitrogen Corp., Carlsbad, Calif., USA.

EXAMPLE 3

Analysis of the AHASL Genes of Four Wheat Genotypes

A sample containing wheat genomic DNA is obtained by any method known in the art for purifying genomic DNA from plant tissues, particularly wheat. However, when comparing two or more wheat plants, an equivalent amount of tissue from each of the plants should be used for the purification of the genomic DNA so as to ensure that samples from each of the plants will contain similar concentrations of genomic DNA. Typically, the DNA concentration of the sample is about 100 ng DNA per µL. If the DNA concentration is greater than this range one should dilute the sample to about 50 ng DNA per µL. While the method of the invention does not depend on a particular DNA concentration, the DNA concentration of the sample is preferably between about 5 and about 100 ng DNA per µL.

The first-round PCR amplification was performed using the Expand High Fidelity PCR System (Roche Applied Science, Indianapolis, Ind., USA). A first round PCR reaction comprising the components set forth in Table 2 was prepared. The Expand High Fidelity PCR System was used because this system comprises, in addition to Taq polymerase, a proof-reading DNA polymerase (Tgo DNA polymerase) that minimizes mutations that may result from the inadvertent incorporation a non-complementary nucleotides. Such PCR-induced mutations could interfere with the second-round PCR amplification described below. Thus, a high-fidelity amplification was desired for the first-round-PCR. Therefore, the use of a PCR system that comprises a proofreading DNA polymerase-such as, for example, the Expand High Fidelity PCR System—was employed for the first-round amplification.

TABLE 2

Components of First-Round PCR Reaction

| Component | Volume (μL) | Final concentration |
|---|---|---|
| Primer CM-F (10 μM) | 0.5 | 0.2 μM |
| Primer CM-R (10 μM) | 0.5 | 0.2 μM |
| 10 X PCR buffer[1] | 2.5 | 1 X |
| $Mg^{2+}$, 25 mM | 2.5 | 2.5 mM |
| Expand High Fidelity Enzyme mix[2] (3.3 u/μL) | 0.5 | 1.7 U/reaction |
| dNTPs (25 mM) | 0.2 | 0.2 mM |
| Genomic DNA | 1 | |
| $H_2O$ | 17.3 | |

[1]Expand High Fidelity buffer, 10X concentration without $MgCl_2$.
[2]Expand High Fidelity Enzyme mix contains Taq DNA polymerase and Tgo DNA polymerase, a thermostable DNA polymerase with proofreading activity.

The first round PCR amplification (also referred to herein above as the "pre-amplification") was performed under in a TGradient Thermocycler (Biometra GmbH, Goettingen, Germany). The following thermocycling conditions were employed sequentially: (1) 94° C. for 3 minutes; (2) 25 cycles of 94° C. for 30 seconds, 56° C. for 1 minute; and 72° C. for 45 seconds; and (3) 72° C. for 7 minutes.

After completion of the first round PCR amplification, an aliquot of the PCR product solution is subjected to digestion with Exonuclease I (Amersham Biosciences Corp., Piscataway, N.J., USA) as follows. To a 2 μL aliquot of the PCR product solution, 0.05 μL ExoI (10 units/μL) and 4.95 μl $H_2O$ were added. The resulting mixture was incubated at 37° C. for 1 hour followed by incubation at 72° C. for 15 minutes. Following the second incubation, the ExoI reaction mixture was diluted sequentially. First, 100 μL of $H_2O$ was added to the ExoI reaction mixture and then mixed. Next, a 10 μL aliquot was removed from the diluted ExoI reaction and further diluting by adding to 190 μL of $H_2O$. A 1 μL aliquot of resulting diluted solution was used as the DNA containing sample for each second round PCR.

The second round PCR amplification can be used to the detect the presence of the mutant and wild-type alleles for each of the three AHASL genes, AHASL1D, AHASL1B, and AHASL1A, if desired. Alternatively, the presence of either a wild-type or mutant allele at a single AHASL gene or two AHASL genes can be determined. Depending on the desired outcome, the second round PCR amplifications may include 1, 2, 3, 4, 5, or 6 separate amplifications employing the six combinations of primers that are set forth in Table 3.

TABLE 3

Second-Round PCR primer for the Detection of Wild-Type and Mutant Alleles of AHASL Genes

| AHASL | Allele | Forward Primer 1 | Forward Primer 2 | Reverse Primer |
|---|---|---|---|---|
| AHASL1D | wild type | 1A, D-F (SEQ ID NO: 5) | WT-F (SEQ ID NO: 4) | 1D-R (SEQ ID NO: 7) |
| AHASL1D | mutant | 1A, D-F (SEQ ID NO: 5) | MU-F (SEQ ID NO: 3) | 1D-R (SEQ ID NO: 7) |
| AHASL1B | wild type | 1B-F (SEQ ID NO: 6) | WT-F (SEQ ID NO: 4) | 1B-R (SEQ ID NO: 8) |
| AHASL1B | mutant | 1B-F (SEQ ID NO: 6) | MU-F (SEQ ID NO: 3) | 1B-R (SEQ ID NO: 8) |
| AHASL1A | wild type | 1A, D-F (SEQ ID NO: 5) | WT-F (SEQ ID NO: 4) | 1A-R (SEQ ID NO: 9) |
| AHASL1A | mutant | 1A, D-F (SEQ ID NO: 5) | MU-F (SEQ ID NO: 3) | 1A-R (SEQ ID NO: 9) |

Second round PCR amplifications were performed using HotStar Taq DNA Polymerase (Qiagen, Inc., Valencia, Calif., USA). A second round PCR reaction comprising the components set forth in Table 4 was prepared for each group of three primers. A "hot start-type" DNA polymerase was selected for the second-round PCR to enhance the probability of amplifying only the desired target sequences.

TABLE 4

Components of Second-Round PCR Reaction

| Component | Volume (μL) | Final concentration |
|---|---|---|
| Forward primer 1 (10 μM) | 0.4 | 0.16 μM |
| Forward primer 2 (10 μM) | 0.5 | 0.2 μM |
| Reverse primer (10 μM) | 0.5 | 0.2 μM |
| dNTPs (25 mM) | 0.2 | 0.2 mM |
| 10X buffer | 2.5 | 1 X |
| Hot Star Taq DNA Polymerase (5 u/μl) | 0.125 | 0.625 U/reaction |
| DNA solution | 1 | |
| $H_2O$ | 19.8 | |

The second-round PCR amplification was performed under in a TGradient Thermocycler (Biometra GmbH, Goettingen, Germany). The following thermocycling conditions were employed sequentially: (1) 95° C. for 15 minutes; (2) eight touchdown cycles with the annealing temperature decreased 1° C. with each successive cycle with the a first cycle of 94° C. for 1 minute, 68° C. (annealing temperature) for 1 minute, and 72° C. for 1 minute, and in cycles 2-8, the annealing temperature was 67° C., 66° C., 65° C., 64° C., 63° C., 62° C., and 61° C., respectively (annealing time of 1 minute for each cycle); (3) 26 cycles of 94° C. for 1 minute, 60° C. for 1 minute, and 72° C., for 1 minute; and (4) a final extension at 72° C. for 10 minutes.

Following the second-round PCR amplification, the second-round PCR products were subjected to agarose gel electrophoresis in a horizontal apparatus by methods known to those of ordinary skill in the art. Following electrophoresis, the gel was subjected to ethidium-bromide staining, and the PCR products detected by florescence in the presence of UV light.

Figure 5:
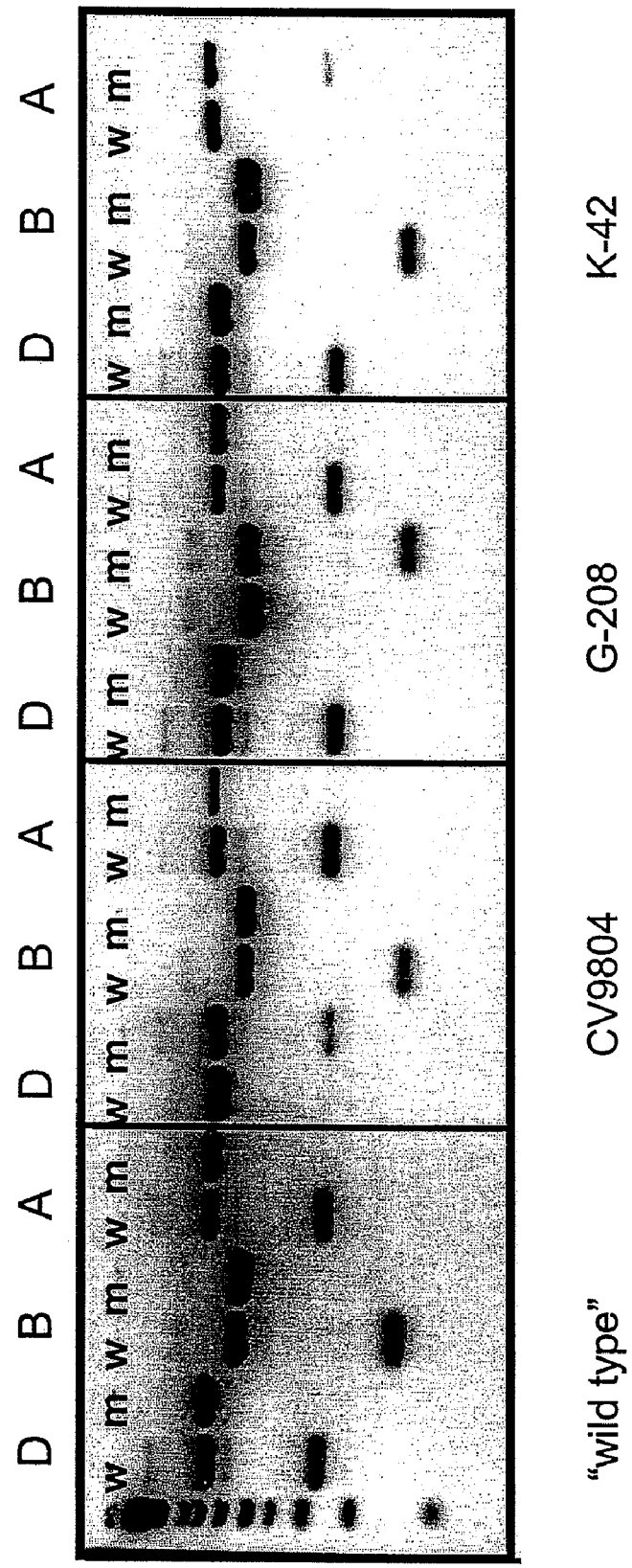
FIG. 5 is a negative photographic image of a single UV-transilluminated, ethidium-bromide-treated agarose gel. Four wheat genotypes were analyzed by all six assays as described in Example 3. The wheat genotypes tested are: Kirschauff (indicated as "wild-type" in FIG. 5), CV9804, G-208, and K-42. Of the four genotypes, CV9804, G-208, and K-42 possess the IMI-tolerance trait. Above the bands the reaction is denoted by a capital letter (above the panels) and by a lower-case letter within the panels. For example the left most pair of bands within each panel is the assay for AHASL1D (D), wild-type allele (w), while the right-most lanes are AHASL1A (A) mutant-allele (m) reactions. The center two lanes in each panel are represent the result of the wild-type allele (w) and the mutant-allele (m) assays for AHASL1B (B). In each lane, the control band is the upper band (longer fragment) and the diagnostic band is the lower (shorter fragment).

FIG. 5 provides an example of the results that were obtained using the methods of the invention with four wheat genotypes, "wild type", CV9804, G-208, and K-42. For each genotype, six second-round PCR amplifications were performed to allow the determination of the zygosity at each of the three AHASL alleles. For example the left-most pair of bands within each panel is the assay for AHASL1D, wild-type allele, while the right-most pair of bands within each panel is the assay for AHASL1A mutant allele. In each lane, the control band is the upper band (about 750 bp for AHASL1D and AHASL1A, and about 580 bp for AHASL1B) and the diagnostic band is the lower band (about 270 bp for AHASL1D and AHASL1A, and about 150 bp for AHASL1B). The control band result was produced by amplification between the forward primer 1 and the reverse primer (see Table 3). The diagnostic band was produced by amplification between the forward primer 2 (WT-F or MU-F). From FIG. 5, one can conclude that CV9804 is homozygous for the mutant allele of AHASL1D, G-208, homozygous for the mutant allele of AHASL1B, and K-42, homozygous for the mutant allele of AHASL1A. These results are in agreement with genotypes determined from standard genetic analyses (data not shown).

The methods described herein above have been tested with wheat plants that are known to be homozygous for the mutant allele, heterozygous, and homozygous for the wild-type allele at each of the wheat AHASL genes. The results of these tests confirm (data not shown) that the methods disclosed herein can be used to rapidly analyze the genome of wheat plants. Thus, the methods of the present invention can be used to rapidly determine whether a particular wheat plant is homozygous for the mutant AHASL allele, heterozygous, or homozygous for the wild-type allele for each of that plant's AHASL genes. Accordingly, the present invention provides methods that can be employed by plant breeders in the production of imidazolinone-tolerant wheat plants having one, two, three, four, five, or six mutant AHASL alleles in their genomes.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A method for detecting a variant allele of a plant acetohydroxyacid synthase large subunit (AHASL) gene that confers tolerance to imidazolinone herbicides on the plant, said method comprising the steps of:
(a) obtaining genomic DNA from the plant;
(b) using said DNA as a template for a PCR amplification comprising said DNA, polymerase, deoxyribonucleotide triphosphates, a forward AHASL-gene-specific primer, a reverse AHASL-gene-specific primer, and a variant-allele specific primer comprising a nucleotide sequence with a 5' end and a 3' end, wherein said nucleotide sequence is capable of annealing to the complement of nucleotides 3 to 23 of SEQ ID NO:12, wherein the 3'-end nucleotide of said nucleotide sequence is cytidine, wherein said cytidine is at the position that corresponds to the site of a G-to-A substitution that gives rise to an S653(At)N substitution in an AHASL protein; and
(c) detecting a product of said PCR amplification, said product corresponding to the region of said AHASL gene bounded by the annealing sites of the variant-allele specific primer and the reverse AHASL-gene-specific primer on said AHASL gene, wherein detecting said product indicates the presence of a variant allele of the plant AHASL gene;
wherein said variant-allele specific primer is 20 nucleotides or more in length and is capable of annealing to a region of an AHASL gene that is nested between the annealing sites of said forward and reverse AHASL-gene-specific primers.

2. The method of claim 1, wherein said forward AHASL-gene-specific primer comprises the sequence set forth in SEQ ID NO:5.

3. The method of claim 1, wherein said reverse AHASL-gene-specific primer has the sequence set forth in SEQ ID NO:9.

4. The method of claim 1, wherein said forward AHASL-gene-specific primer comprises the sequence set forth in SEQ ID NO:5 and said reverse AHASL-gene-specific primer has the sequence set forth in SEQ ID NO:9.

5. The method of claim 1, wherein said variant-allele specific primer comprises SEQ ID NO:3.

6. The method of claim 1, wherein said DNA has been subjected to a pre-amplification before step (b), said pre-amplification comprising said DNA, polymerase, deoxyribonucleotide triphosphates, a forward AHASL primer, and a reverse AHASL primer, wherein said forward and reverse AHASL-gene-specific primers are capable of annealing to regions of an AHASL gene that are nested between the annealing sites of said forward and reverse AHASL primers.

7. The method of claim 6, wherein said DNA is digested with exonuclease following said pre-amplification and before step (b).

8. The method of claim 6, wherein said forward AHASL primer and said reverse AHASL primer are designed to anneal to a Triticum AHASL1A, AHASL1B, and AHASL1D.

9. The method of claim 6, wherein said forward AHASL primer comprises the nucleotide sequence set forth in SEQ ID NO:1.

10. The method of claim 6, wherein said reverse AHASL primer comprises the nucleotide sequence set forth in SEQ ID NO:2.

11. The method of claim 6, wherein said forward AHASL primer comprises the nucleotide sequence set forth in SEQ ID NO:1 and said reverse AHASL primer comprises the nucleotide sequence set forth in SEQ ID NO:2.

12. The method of claim 1 further comprising:
using said DNA as a template for a second PCR amplification comprising said DNA, polymerase, deoxyribonucleotide triphosphates, said forward AHASL-gene-specific primer, said reverse AHASL-gene-specific primer, and a wild-type-allele-specific primer comprising a second nucleotide sequence with a 5' end and a 3' end, wherein said second nucleotide sequence is capable of specific annealing to the complement of nucleotides 4 to 23 of SEQ ID NO:10, wherein the 3'-end nucleotide of said second nucleotide sequence is guanosine, wherein said guanosine is at the position that corresponds to the site of the G-to-A substitution that gives rise to the S653(At)N substitution in an AHASL protein
wherein said wild-type-allele-specific primer is 20 nucleotides or more in length and is capable of specific annealing to a region of an AHASL gene that is nested between the annealing sites of said forward and reverse AHASL-gene-specific primers.

13. The method of claim 12, wherein said wild-type-allele-specific primer comprises the nucleotide sequence set forth in SEQ ID NO:4.

14. The method of claim 12, wherein said forward AHASL-gene-specific primer has the sequence set forth in SEQ ID NO:5 and said reverse AHASL-gene-specific primer has the sequence set forth in SEQ ID NO:9.

15. The method of claim 12 further comprising: using said DNA as a template in a pre-amplification comprising said DNA, deoxyribonucleotide triphosphates, polymerase, a forward AHASL primer, and a reverse AHASL primer, so as to produce pre-amplified DNA.

16. The method of claim 15, wherein said pre-amplified DNA is digested with exonuclease before step (c).

17. The method of claim 1, wherein the plant is wheat, rice, barley, rye, or triticale.

18. The method of claim 1, wherein the plant is wheat.

19. A method for determining zygosity of a plant AHASL gene, the method comprising:
  (a) conducting a first PCR amplification from a DNA template that comprises a plant AHASL gene, using a forward AHASL-gene-specific primer, a reverse AHASL-gene-specific primer, and a variant-allele specific primer, wherein the variant-allele specific primer comprises a nucleotide sequence with a 5' end and a 3' end, wherein said nucleotide sequence is capable of annealing to the complement of nucleotides 3 to 23 of SEQ ID NO:12, wherein the 3'-end nucleotide of said nucleotide sequence is cytidine, wherein said cytidine is at the position that corresponds to the site of a G-to-A substitution that gives rise to an S653(At)N substitution in an AHASL protein, wherein said variant-allele specific primer is 20 nucleotides or more in length and is capable of annealing to a region of an AHASL gene that is nested between the annealing sites of said forward and reverse AHASL-gene-specific primers; and
  (b) conducting a second PCR amplification performed using said DNA template, said forward AHASL-gene-specific primer, said reverse AHASL-gene-specific primer, and a wild-type-allele-specific primer;
wherein comparison of the results of (a) and (b) indicates the zygosity.

20. The method of claim 19, wherein the wild-type-allele-specific primer comprises a nucleotide sequence that is 20 nucleotides or more in length and is capable of annealing to the complement of nucleotides 3 to 23 of SEQ ID NO:12, wherein the 3'-end nucleotide of said nucleotide sequence is guanosine, wherein said guanosine is at the position that corresponds to the site of a G-to-A substitution that gives rise to an S653(At)N substitution in an AHASL protein, wherein said nucleotide sequence comprises a nucleotide that is a mismatch to the nucleotide at the position, in a polynucleotide encoding said AHASL protein, that corresponds to position 20 of SEQ ID NO:12.

21. The method of claim 20, wherein said mismatched nucleotide is a G.

22. The method of claim 19, wherein said variant-allele specific primer comprises the nucleotide sequence shown as SEQ ID NO:3.

23. The method of claim 19, wherein said wild-type-allele-specific primer comprises the nucleotide sequence shown as SEQ ID NO:4.

24. The method of claim 19, wherein the plant is wheat, rice, barley, rye, or triticale.

25. The method of claim 19, wherein the plant is wheat.

* * * * *

```
                              SEQUENCE LISTING

<160> NUMBER OF SEQ ID NOS: 27

<210> SEQ ID NO 1
<211> LENGTH: 21
<212> TYPE: DNA
<213> ORGANISM: Artificial Sequence
<220> FEATURE:
<223> OTHER INFORMATION: Primer CM-F

<400> SEQUENCE: 1
ccgccgcaat atgctatcca g                                              21

<210> SEQ ID NO 2
<211> LENGTH: 21
<212> TYPE: DNA
<213> ORGANISM: Artificial Sequence
<220> FEATURE:
<223> OTHER INFORMATION: Primer CM-R

<400> SEQUENCE: 2
gtaggacaag aaacttgcat g                                              21

<210> SEQ ID NO 3
<211> LENGTH: 21
<212> TYPE: DNA
<213> ORGANISM: Artificial Sequence
<220> FEATURE:
<223> OTHER INFORMATION: Primer MU-F

<400> SEQUENCE: 3
cgtgctgcct atgatccgaa c                                              21

<210> SEQ ID NO 4
<211> LENGTH: 20
<212> TYPE: DNA
<213> ORGANISM: Artificial Sequence
<220> FEATURE:
<223> OTHER INFORMATION: Primer WT-F

<400> SEQUENCE: 4
gtgctgccta tgatccgaag                                                20
```

```
<210> SEQ ID NO 5
<211> LENGTH: 20
<212> TYPE: DNA
<213> ORGANISM: Artificial Sequence
<220> FEATURE:
<223> OTHER INFORMATION: Primer 1A,D-F

<400> SEQUENCE: 5
gggaggcgat cattgccact                                              20

<210> SEQ ID NO 6
<211> LENGTH: 20
<212> TYPE: DNA
<213> ORGANISM: Artificial Sequence
<220> FEATURE:
<223> OTHER INFORMATION: Primer 1B-F

<400> SEQUENCE: 6
ggcagtggct gtcttcatcc                                              20

<210> SEQ ID NO 7
<211> LENGTH: 24
<212> TYPE: DNA
<213> ORGANISM: Artificial Sequence
<220> FEATURE:
<223> OTHER INFORMATION: Primer 1D-R

<400> SEQUENCE: 7
gcacatccct acaaaagaga agat                                         24

<210> SEQ ID NO 8
<211> LENGTH: 24
<212> TYPE: DNA
<213> ORGANISM: Artificial Sequence
<220> FEATURE:
<223> OTHER INFORMATION: Primer 1B-R

<400> SEQUENCE: 8
cagtagttga tacaacacgc aggt                                         24

<210> SEQ ID NO 9
<211> LENGTH: 25
<212> TYPE: DNA
<213> ORGANISM: Artificial Sequence
<220> FEATURE:
<223> OTHER INFORMATION: Primer 1A-R

<400> SEQUENCE: 9
gacagcacat ccctacaaaa gatag                                        25

<210> SEQ ID NO 10
<211> LENGTH: 42
<212> TYPE: DNA
<213> ORGANISM: Triticum aestivum
<220> FEATURE:
<221> NAME/KEY: misc_feature
<222> LOCATION: (0)...(0)
<223> OTHER INFORMATION: Wild type AHASL1D
<221> NAME/KEY: CDS
<222> LOCATION: (1)...(42)

<400> SEQUENCE: 10 cac gtg ctg cct atg atc cca agc ggt ggt gct ttc aag gac            42
His Val Leu Pro Met Ile Pro Ser Gly Gly Ala Phe Lys Asp
1               5                   10

<210> SEQ ID NO 11
```

```
<211> LENGTH: 14
<212> TYPE: PRT
<213> ORGANISM: Triticum aestivum

<400> SEQUENCE: 11

His Val Leu Pro Met Ile Pro Ser Gly Gly Ala Phe Lys Asp
1               5                   10

<210> SEQ ID NO 12
<211> LENGTH: 42
<212> TYPE: DNA
<213> ORGANISM: Triticum aestivum
<220> FEATURE:
<221> NAME/KEY: misc_feature
<222> LOCATION: (0)...(0)
<223> OTHER INFORMATION: Mutant AHASL1D
<221> NAME/KEY: CDS
<222> LOCATION: (1)...(42)

<400> SEQUENCE: 12 cac gtg ctg cct atg atc cca aac ggt ggt gct ttc aag gac         42
His Val Leu Pro Met Ile Pro Asn Gly Gly Ala Phe Lys Asp
1               5                   10

<210> SEQ ID NO 13
<211> LENGTH: 14
<212> TYPE: PRT
<213> ORGANISM: Triticum aestivum

<400> SEQUENCE: 13

His Val Leu Pro Met Ile Pro Asn Gly Gly Ala Phe Lys Asp
1               5                   10

<210> SEQ ID NO 14
<211> LENGTH: 42
<212> TYPE: DNA
<213> ORGANISM: Triticum aestivum
<220> FEATURE:
<221> NAME/KEY: misc_feature
<222> LOCATION: (0)...(0)
<223> OTHER INFORMATION: Wild type AHASL1B
<221> NAME/KEY: CDS
<222> LOCATION: (1)...(42)

<400> SEQUENCE: 14 cac gtg ctg cct atg atc cca agc ggt ggt gct ttt aag gac         42
His Val Leu Pro Met Ile Pro Ser Gly Gly Ala Phe Lys Asp
1               5                   10

<210> SEQ ID NO 15
<211> LENGTH: 14
<212> TYPE: PRT
<213> ORGANISM: Triticum aestivum

<400> SEQUENCE: 15

His Val Leu Pro Met Ile Pro Ser Gly Gly Ala Phe Lys Asp
1               5                   10

<210> SEQ ID NO 16
<211> LENGTH: 42
<212> TYPE: DNA
<213> ORGANISM: Triticum aestivum
<220> FEATURE:
<221> NAME/KEY: misc_feature
<222> LOCATION: (0)...(0)
<223> OTHER INFORMATION: Mutant AHASL1B
<221> NAME/KEY: CDS
<222> LOCATION: (1)...(42)

<400> SEQUENCE: 16
```

```
cac gtg ctg cct atg atc cca aac ggt ggt gct ttt aag gac          42
His Val Leu Pro Met Ile Pro Asn Gly Gly Ala Phe Lys Asp
1               5                   10
```

<210> SEQ ID NO 17
<211> LENGTH: 14
<212> TYPE: PRT
<213> ORGANISM: Triticum aestivum

<400> SEQUENCE: 17

```
His Val Leu Pro Met Ile Pro Asn Gly Gly Ala Phe Lys Asp
1               5                   10
```

<210> SEQ ID NO 18
<211> LENGTH: 42
<212> TYPE: DNA
<213> ORGANISM: Triticum aestivum
<220> FEATURE:
<221> NAME/KEY: misc_feature
<222> LOCATION: (0)...(0)
<223> OTHER INFORMATION: Wild type AHASL1A
<221> NAME/KEY: CDS
<222> LOCATION: (1)...(42)

<400> SEQUENCE: 18

```
cac gtg ctg cct atg atc cca agc ggt ggt gct ttc aag gac          42
His Val Leu Pro Met Ile Pro Ser Gly Gly Ala Phe Lys Asp
1               5                   10
```

<210> SEQ ID NO 19
<211> LENGTH: 14
<212> TYPE: PRT
<213> ORGANISM: Triticum aestivum

<400> SEQUENCE: 19

```
His Val Leu Pro Met Ile Pro Ser Gly Gly Ala Phe Lys Asp
1               5                   10
```

<210> SEQ ID NO 20
<211> LENGTH: 42
<212> TYPE: DNA
<213> ORGANISM: Triticum aestivum
<220> FEATURE:
<221> NAME/KEY: misc_feature
<222> LOCATION: (0)...(0)
<223> OTHER INFORMATION: Mutant AHASL1A
<221> NAME/KEY: CDS
<222> LOCATION: (1)...(42)

<400> SEQUENCE: 20

```
cac gtg ctg cct atg atc cca aac ggt ggt gct ttc aag gac          42
His Val Leu Pro Met Ile Pro Asn Gly Gly Ala Phe Lys Asp
1               5                   10
```

<210> SEQ ID NO 21
<211> LENGTH: 14
<212> TYPE: PRT
<213> ORGANISM: Triticum aestivum

<400> SEQUENCE: 21

```
His Val Leu Pro Met Ile Pro Asn Gly Gly Ala Phe Lys Asp
1               5                   10
```

<210> SEQ ID NO 22
<211> LENGTH: 983
<212> TYPE: DNA
<213> ORGANISM: Triticum aestivum
<220> FEATURE:

<220> FEATURE:
<221> NAME/KEY: misc_feature
<222> LOCATION: (0)...(0)
<223> OTHER INFORMATION: AHASL1B

<400> SEQUENCE: 22

| | | |
|---|---|---|
| tttggtccat ggcacaagga gttggatcag cagaagaggg agtttcctct aggattcaag | 60 |
| acttttggtg aggccatccc gccgcaatat gctatccagg tactggatga gctgacaaaa | 120 |
| ggggaggcga tcattgccac cggtgttggg cagcatcaga tgtgggcggc tcagtattac | 180 |
| acttacaagc ggccacggca gtggctgtct tcatccggtt tgggtgcaat gggatttggg | 240 |
| ttgccagctg cagctggcgc tgctgtggcc aacccaggtg ttacagttgt tgacattgat | 300 |
| ggggatggta gtttcctcat gaacattcag gagttggcgt tgatccgtat tgagaacctc | 360 |
| ccagtgaagg tgatgatatt gaacaaccag catctgggaa tggtggtgca gtgggaggat | 420 |
| aggttttaca aggccaaccg ggcgcacaca taccttggca acccagaaaa tgagagtgag | 480 |
| atatatccag attttgtgac gattgctaaa ggattcaacg ttccggcagt tcgtgtgacg | 540 |
| aagaagagcg aagtcactgc agcaatcaag aagatgcttg acccccagg gccatacttg | 600 |
| ttggatatca ttgtcccgca tcaggagcac gtgctgccta tgatcccaag cggtggtgct | 660 |
| tttaaggaca tgatcatgga gggtgatggc aggacctcgt actgaaattt cgacctacaa | 720 |
| gacctacaag tgtgacatgc gcaatcagca tgatacctgc gtgttgtatc aactactggg | 780 |
| ggttcaactg tgaaccatgc gttttctagt ttgcttgttt cattcatata agcttgtgtt | 840 |
| acttagttcc gaaccgtgta gttttgtagt ctctgttctc ttttgtaggg aygtgctgtc | 900 |
| ataaratatc atgcaagttt cttgtcctac atatcaataa taagcacttc catggagcaa | 960 |
| aaaaaaaaaa aaaaaaaaaa aaa | 983 |

<210> SEQ ID NO 23
<211> LENGTH: 983
<212> TYPE: DNA
<213> ORGANISM: Triticum aestivum
<220> FEATURE:
<221> NAME/KEY: misc_feature
<222> LOCATION: (0)...(0)
<223> OTHER INFORMATION: AHASL1D

<400> SEQUENCE: 23

| | | |
|---|---|---|
| tttggtccat ggcacaagga gttggatcag cagaagaggg agtttcctct aggattcaag | 60 |
| acttttggcg aggccatccc gccgcaatat gctatccagg tactggatga gctgacaaaa | 120 |
| ggggaggcga tcattgccac tggtgttggg cagcaccaga tgtgggcggc tcagtattac | 180 |
| acttacaagc ggccacggca gtggctgtct tcgtctggtt tgggggcaat gggatttggg | 240 |
| ttaccagctg cagctggcgc tgctgtggcc aacccaggtg ttacagttgt tgacattgat | 300 |
| ggtgatggta gtttcctcat gaacattcag gagttggcgt tgatccgcat tgagaacctc | 360 |
| ccagtgaagg tgatgatatt gaacaaccag catctgggaa tggtggtgca gtgggaggat | 420 |
| aggttttaca aggccaatcg ggcgcacaca taccttggca acccagaaaa tgagagtgag | 480 |
| atatatccag attttgtgac gattgctaaa ggattcaacg ttccagcagt tcgagtgacg | 540 |
| aagaagagcg aagtcactgc agcaatcaag aagatgcttg acccccagg gccatacttg | 600 |
| ttggatatca tagtcccgca tcaggagcac gtgctgccta tgatcccaag cggtggtgct | 660 |
| ttcaaggaca tgatcatgga gggtgatggc aggacctcgt actgaaattt cgacctacaa | 720 |
| gacctacaag tgtgacatgc gcaatcagca tgatgcccgc gtgttgtatc aactactagg | 780 |
| ggttcaactg tgarccatgc gttttctagt ttgcttgttt cattcatata agcttgtrtt | 840 |

```
acttagttcc gaaccctgta gttttgtagt ctatgttctc ttttgtaggg atgtgctgtc      900
ataaratrtc atgcaagttt cttgtcctac atatcaataa taagtacttc catgcagtaa      960
aaaaaaaaaa aaaaaaaaaa aaa                                              983
```

```
<210> SEQ ID NO 24
<211> LENGTH: 983
<212> TYPE: DNA
<213> ORGANISM: Triticum aestivum
<220> FEATURE:
<221> NAME/KEY: misc_feature
<222> LOCATION: (0)...(0)
<223> OTHER INFORMATION: AHASL1A

<400> SEQUENCE: 24
```

```
tttggtccat ggcacaagga gttggatcag cagaagaggg agtttcctct aggattcaag       60
acttttggcg aggccatccc gccgcaatat gctatccagg tactggatga gctgacaaaa      120
ggggaggcga tcattgctac tggtgttggg cagcaccaga gtgggcggc tcagtattac       180 acttacaagc ggccacggca gtggctgtct tcgtctggtt tgggggcaat gggatttggg      240
ttaccagctg cagctggcgc tgctgtggcc aacccaggtg ttacagttgt tgacattgat      300
ggagatggta gtttcctcat gaacattcag gagttggcat tgatccgtat tgagaacctc      360
cctgtgaagg tgatgatatt gaacaaccag catctgggaa tggtggtgca atggaggat      420 aggttttaca aggccaatcg ggcgcacaca taccttggca acccagaaaa tgagagtgag      480
atatatccag attttgtgac gattgctaaa ggattcaacg ttccggcagt tcgtgtgacg      540
aagaagagcg aagtcactgc agcaatcaag aagatgcttg agaccccagg gccatacttg      600
ttggatatca tcgtcccgca tcaggagcac gtgctgccta tgatcccaag cggtggtgct      660
ttcaaggaca tgatcatgga gggtgatggc aggacctcgt actgaaattt cgacctacaa      720
gacctacaag tgtgacatgc gcaatcagca tggtgcccgc gtgttgtatc aactactagg      780
ggttcaactg tgaaccatgc gttttctagt ttgcttgttt cattcatata agcttgtgtt      840
acttagttcc gaaccctgta gctttgtagt ctatgctatc ttttgtaggg atgtgctgtc      900
ataaaatatc atgcaagttt cttgtcctac atatcaataa taagtacttc catggaaaaa      960
aaaaaaaaaa aaaaaaaaaa aaa                                              983
```

```
<210> SEQ ID NO 25
<211> LENGTH: 933
<212> TYPE: DNA
<213> ORGANISM: Triticum aestivum
<220> FEATURE:
<221> NAME/KEY: misc_feature
<222> LOCATION: (0)...(0)
<223> OTHER INFORMATION: AHASL1B

<400> SEQUENCE: 25
```

```
aggattcaag acttttggtg aggccatccc gccgcaatat gctatccagg tactggatga       60
gctgacaaaa ggggaggcga tcattgccac cggtgttggg cagcatcaga gtgggcggc      120 tcagtattac acttacaagc ggccacggca gtggctgtct tcatccggtt tgggtgcaat      180
gggatttggg ttgccagctg cagctggcgc tgctgtggcc aacccaggtg ttacagttgt      240
tgacattgat ggggatggta gtttcctcat gaacattcag gagttggcgt tgatccgtat      300
tgagaacctc ccagtgaagg tgatgatatt gaacaaccag catctgggaa tggtggtgca      360
gtgggaggat aggttttaca aggccaaccg ggcgcacaca taccttggca acccagaaaa      420
tgagagtgag atatatccag attttgtgac gattgctaaa ggattcaacg ttccggcagt      480
```

```
tcgtgtgacg aagaagagcg aagtcactgc agcaatcaag aagatgcttg agacccccagg    540 gccatacttg ttggatatca ttgtcccgca tcaggagcac gtgctgccta tgatcccaag    600
cggtggtgct tttaaggaca tgatcatgga gggtgatggc aggacctcgt actgaaattt    660
cgacctacaa gacctacaag tgtgacatgc gcaatcagca tgatacctgc gtgttgtatc    720
aactactggg ggttcaactg tgaaccatgc gttttctagt ttgcttgttt cattcatata    780
agcttgtgtt acttagttcc gaaccgtgta gttttgtagt ctctgttctc ttttgtaggg    840
aygtgctgtc ataaratatc atgcaagttt cttgtcctac atatcaataa taagcacttc    900
catggagcaa aaaaaaaaaa aaaaaaaaaa aaa                                 933
```

<210> SEQ ID NO 26
<211> LENGTH: 933
<212> TYPE: DNA
<213> ORGANISM: Triticum aestivum
<220> FEATURE:
<221> NAME/KEY: misc_feature
<222> LOCATION: (0)...(0)
<223> OTHER INFORMATION: AHASL1D

<400> SEQUENCE: 26

```
aggattcaag acttttggcg aggccatccc gccgcaatat gctatccagg tactggatga     60
gctgacaaaa ggggaggcga tcattgccac tggtgttggg cagcaccaga gtgggcggc    120 tcagtattac acttacaagc ggccacggca gtggctgtct tcgtctggtt tgggggcaat    180
gggatttggg ttaccagctg cagctggcgc tgctgtggcc aacccaggtg ttacagttgt    240
tgacattgat ggtgatggta gtttcctcat gaacattcag gagttggcgt tgatccgcat    300
tgagaacctc ccagtgaagg tgatgatatt gaacaaccag catctgggaa tggtggtgca    360
gtgggaggat aggttttaca aggccaatcg ggcgcacaca taccttggca acccagaaaa    420
tgagagtgag atatatccag attttgtgac gattgctaaa ggattcaacg ttccagcagt    480
tcgagtgacg aagaagagcg aagtcactgc agcaatcaag aagatgcttg acccccagg    540 gccatacttg ttggatatca tagtcccgca tcaggagcac gtgctgccta tgatcccaag    600
cggtggtgct ttcaaggaca tgatcatgga gggtgatggc aggacctcgt actgaaattt    660
cgacctacaa gacctacaag tgtgacatgc gcaatcagca tgatgcccgc gtgttgtatc    720
aactactagg ggttcaactg tgarccatgc gttttctagt ttgcttgttt cattcatata    780
agcttgtrtt acttagttcc gaaccctgta gttttgtagt ctatgttctc ttttgtaggg    840
atgtgctgtc ataaratrtc atgcaagttt cttgtcctac atatcaataa taagtacttc    900
catgcagtaa aaaaaaaaaa aaaaaaaaaa aaa                                 933
```

<210> SEQ ID NO 27
<211> LENGTH: 933
<212> TYPE: DNA
<213> ORGANISM: Triticum aestivum
<220> FEATURE:
<221> NAME/KEY: misc_feature
<222> LOCATION: (0)...(0)
<223> OTHER INFORMATION: AHASL1A

<400> SEQUENCE: 27

```
aggattcaag acttttggcg aggccatccc gccgcaatat gctatccagg tactggatga     60
gctgacaaaa ggggaggcga tcattgctac tggtgttggg cagcaccaga gtgggcggc    120 tcagtattac acttacaagc ggccacggca gtggctgtct tcgtctggtt tgggggcaat    180
gggatttggg ttaccagctg cagctggcgc tgctgtggcc aacccaggtg ttacagttgt    240
```

```
tgacattgat ggagatggta gtttcctcat gaacattcag gagttggcat tgatccgtat      300
tgagaacctc cctgtgaagg tgatgatatt gaacaaccag catctgggaa tggtggtgca      360
atgggaggat aggtttaca aggccaatcg ggcgcacaca taccttggca acccagaaaa      420
tgagagtgag atatatccag attttgtgac gattgctaaa ggattcaacg ttccggcagt      480
tcgtgtgacg aagaagagcg aagtcactgc agcaatcaag aagatgcttg agacccagg      540 gccatacttg ttggatatca tcgtcccgca tcaggagcac gtgctgccta tgatcccaag      600
cggtggtgct ttcaaggaca tgatcatgga gggtgatggc aggacctcgt actgaaattt      660
cgacctacaa gacctacaag tgtgacatgc gcaatcagca tggtgcccgc gtgttgtatc      720
aactactagg ggttcaactg tgaaccatgc gtttctagt ttgcttgttt cattcatata      780
agcttgtgtt acttagttcc gaaccctgta gctttgtagt ctatgctatc ttttgtaggg      840
atgtgctgtc ataaaatatc atgcaagttt cttgtcctac atatcaataa taagtacttc      900
catggaaaaa aaaaaaaaa aaaaaaaaaa aaa                                    933
```